United States Patent
Armstrong

(10) Patent No.: US 9,114,178 B2
(45) Date of Patent: *Aug. 25, 2015

(54) METHODS AND COMPOSITIONS FOR TREATMENT OF MYOTONIC DYSTROPHY

(71) Applicant: Valerion Therapeutics, LLC, Concord, MA (US)

(72) Inventor: Dustin D. Armstrong, Everett, MA (US)

(73) Assignee: Valerion Therapeutics, LLC, Concord, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,517

(22) Filed: Dec. 9, 2013

(65) Prior Publication Data

US 2014/0178377 A1 Jun. 26, 2014

Related U.S. Application Data

(63) Continuation of application No. 12/589,118, filed on Oct. 15, 2009, now Pat. No. 8,609,615.

(60) Provisional application No. 61/196,142, filed on Oct. 15, 2008.

(51) Int. Cl.
| | |
|---|---|
| *C07K 19/00* | (2006.01) |
| *C12N 15/62* | (2006.01) |
| *A61K 47/48* | (2006.01) |
| *C07K 14/47* | (2006.01) |
| *C07K 16/00* | (2006.01) |
| *A61K 38/00* | (2006.01) |

(52) U.S. Cl.
CPC ........... *A61K 47/48415* (2013.01); *C07K 14/47* (2013.01); *C07K 14/471* (2013.01); *C07K 16/00* (2013.01); *A61K 38/00* (2013.01)

(58) Field of Classification Search
CPC ................................ A61K 38/00; C07K 14/47
See application file for complete search history.

(56) References Cited

U.S. PATENT DOCUMENTS

| | | | |
|---|---|---|---|
| 5,622,699 A | 4/1997 | Ruoslahti et al. | |
| 6,068,829 A | 5/2000 | Ruoslahti et al. | |
| 6,174,687 B1 | 1/2001 | Rajotte et al. | |
| 6,180,084 B1 | 1/2001 | Ruoslahti et al. | |
| 6,232,287 B1 | 5/2001 | Ruoslahti et al. | |
| 6,296,832 B1 | 10/2001 | Ruoslahti et al. | |
| 6,303,573 B1 | 10/2001 | Ruoslahti et al. | |
| 6,306,365 B1 | 10/2001 | Ruoslahti et al. | |
| 7,189,396 B1 | 3/2007 | Weisbart | |
| 7,863,017 B2 | 1/2011 | Ervasti et al. | |
| 8,609,615 B2 | 12/2013 | Armstrong | |
| 2008/0292618 A1 | 11/2008 | Weisbart | |
| 2010/0143358 A1 | 6/2010 | Weisbart | |

FOREIGN PATENT DOCUMENTS

| | | |
|---|---|---|
| WO | WO-97/32602 A1 | 9/1997 |
| WO | WO-98/53804 A1 | 12/1998 |
| WO | WO-2008/091911 A2 | 7/2008 |
| WO | WO-2008/148063 A1 | 12/2008 |
| WO | WO-2010/138769 A1 | 12/2010 |

OTHER PUBLICATIONS

Abhinandan, K. R., et al., "Analyzing the "Degree of Humanness" of Antibody Sequences," Journal of Mol. Biol., 369:852-862 (2007).
Ashizawa et al., "Somatic instability of CTG repeat in myotonic dystrophy," Neurology, vol. 43(12), pp. 2674-2678 (1993).
Cooper, Thomas A., "A Reversal of Misfortune of Myotonic Dystrophy?," New England Journal of Medicine, vol. 355(17), pp. 1825-1827 (2006).
Dansithong et al., "MBNL1 is the Primary of Determinant of Focus Formation and Aberrant Insulin Receptor Splicing in DM1," The Journal of Biological Chemistry, vol. 280(7), pp. 5773-5780 (2005).
de Haro et al., "MBNL1 and CUGBP1 Modify Expended CUG-induced Toxicity in a *Drosophila* Model of Myotonic Dystrophy Type 1," Human Molecular Genetics, vol. 15(13): 2138-2145 (2006).
Derossi et al., "The Third Helix of the Antennapedia Homeodomain Translocates through Biological Membranes," The Journal of Biological Chemistry, vol. 269(14), pp. 10444-10450 (1994).
Fardaei et al., "Three proteins, MBNL, MBLL and MBXL, co-localize in vivo with nuclear foci of expanded-repeat transcripts in DM1 and DM2 cells," Human Molecular Genetics, vol. 11(7), pp. 805-814 (2002).
Hansen et al., "Antibody-Mediated Transduction of Therapeutic Proteins Into Living Cells," TheScientificWorld Journal, vol. 5: 782-788 (2005).
Hansen et al., "Intranuclear Protein Transduction through a Nucleoside Salvage Pathway," Journal of Biological Chemistry, vol. 282(29), pp. 20790-20793 (2007).
Hansen, J. E., et al., "Antibody-Mediated Hsp70 Protein Therapy," Brain Research, 1088:187-196 (2006).
Hao, et al., "Muscleblind-like 2 (Mbnl2)—Deficient Mice as a Model for Myotonic Dystrophy," Developmental Dynamics, vol. 237(2), pp. 403-410 (2008).
Ho et al., "Colocalization of muscleblind with RNA foci is separable from mis-regulation of alternative splicing in myotonic dystrophy," Journal of Cell Science, vol. 118(13), pp. 2923-2933 (2005).
Holt et al., "Muscleblind-Like Proteins: Similarities and Differences in Normal and Myotonic Dystrophy Muscle," American Journal of Pathology, vol. 174(1), pp. 216-227 (2009).
Kanadia et al., "A Muscleblind Knockout Model for Myotonic Dystrophy," Science, vol. 302(5652), pp. 1978-1980 (2003).
Kanadia et al., "Reversal of RNA missplicing and myotonia after muscleblind overexpression in a mouse poly(CUG) model for myotonic dystrophy," Proceedings of the National Academy of Sciences USA, vol. 103(31), pp. 11748-11753 (2006).
Kino et al., "Muscleblind protein, MBNL1/EXP, binds specifically to CHHG repeats," Human Molecular Genetics, vol. 13(5), pp. 495-507 (2004).
Korade-Mirnics, et al., "Myotonic dystrophy: molecular windows on a complex etiology," Nucleic Acids Research, vol. 26(6), pp. 1363-1368 (1998).

(Continued)

*Primary Examiner* — John Ulm
(74) *Attorney, Agent, or Firm* — Ropes & Gray LLP

(57) ABSTRACT

In certain embodiments, the present invention provides compositions and methods for treating myotonic dystrophy.

56 Claims, No Drawings

(56) References Cited

OTHER PUBLICATIONS

Lin et al., "Failure of MBLN1-dependent post-natal splicing transitions in myotonic dystrophy," Human Molecular Genetics, vol. 15(13), pp. 2087-2097 (2006).
Liguori et al., "Myotonic Dystrophy Type 2 Caused by a CCTG Expansion in Intron 1 of ZNF9," Science, vol. 293, pp. 864-867 (2001).
Mankodi et al., "Myotonic Dystrophy in Transgenic Mice Expressing an Expanded CUG Repeat," Science, vol. 289, pp. 1769-1773 (2000).
Mankodi et al., "Nuclear RNA Foci in the Heart in Myotonic Dystrophy," Circulation Research, vol. 97(11), pp. 1152-1155 (2005).
Mankodi, A., et al., "Expanded CUG Repeats Trigger Aberrant Splicing of ClC-1 Chloride Channel Pre-mRNA and Hyperexcitability of Skeletal Muscle in Myotonic Dystrophy," Molecular Cell, 10:35-44 (2002).
Miller et al., "Recruitment of human muscleblind proteins to $(CUG)_n$ expansions associated with myotonic dystrophy," The EMBO Journal, vol. 19(17), pp. 4439-4448 (2000).
NCBI GenBank Accession No. NM_018388 dated Feb. 15, 2009.
NCBI GenBank Accession No. NM_018388 dated Jul. 4, 2000.
NCBI GenBank Accession No. NM_021038 dated Dec. 27, 2009.
NCBI GenBank Accession No. NM_021038 dated Oct. 3, 2000.
NCBI GenBank Accession No. NM_133486 dated Feb. 15, 2009.
NCBI GenBank Accession No. NM_133486 dated May 2, 2003.
NCBI GenBank Accession No. NM_144778 dated Aug. 16, 2009.
NCBI GenBank Accession No. NM_144778 dated Jun. 18, 2002.
NCBI GenBank Accession No. NM_207292 dated Apr. 20, 2004.
NCBI GenBank Accession No. NM_207292 dated Jan. 31, 2010.
NCBI GenBank Accession No. NM_207293 dated Apr. 20, 2004.
NCBI GenBank Accession No. NM_207293 dated Dec. 27, 2009.
NCBI GenBank Accession No. NM_207294 dated Apr. 20, 2004.
NCBI GenBank Accession No. NM_207294 dated Jan. 31, 2010.
NCBI GenBank Accession No. NM_207295 dated Apr. 20, 2004.
NCBI GenBank Accession No. NM_207295 dated Dec. 27, 2009.
NCBI GenBank Accession No. NM_207296 dated Apr. 20, 2004.
NCBI GenBank Accession No. NM_207296 dated Jan. 31, 2010.
NCBI GenBank Accession No. NM_207297 dated Apr. 20, 2004.
NCBI GenBank Accession No. NM_207297 dated Dec. 27, 2009.
NCBI GenBank Accession No. NM_207304 dated Apr. 20, 2004.
NCBI GenBank Accession No. NM_207304 dated Jan. 31, 2010.
O'Donnell et al., "A Decade of Molecular Studies of Fragile X Syndrome," Annu. Rev. Neurosci., vol. 25, pp. 315-338 (2002).
Orengo et al., "Expanded CTG repeats within the DMPK 3' UTR causes severe skeletal muscle wasting in an inducible mouse model for myotonic dystrophy," PNAS, vol. 105(7), pp. 2646-2651 (2008).
Osborne et al., "Transcriptional and post-transcriptional impact of toxic RNA in myotonic dystrophy," Human Molecular Genetics, vol. 18(8), pp. 1471-1481 (2009).
Pascual et al., "The Muscleblind family of proteins: an emerging class of regulators of developmentally programmed alternative splicing," Differentiation, vol. 74(2-3), pp. 65-80 (2006).
Pennycooke, M., et al., "Differential Expression of Human Nucleoside Transporters in Normal and Tumor Tissue," Biochemical and Biophysical Research Communications, 280:951-959 (2001).
Ranum et al., "Dominantly inherited, non-coding microsatellite expansion disorders," Current Opinion in Genetics & Development, vol. 12, pp. 266-271 (2002).
Saleem et al., "Association of CAG repeat loci on chromosome 22 with schizophrenia and bipolar disorder," Molecular Psychiatry, vol. 6(6), pp. 694-700 (2001).
Vicente et al., "Muscleblind isoforms are functionally distinct and regulate α-actinin splicing," Differentiation, vol. 75(5), pp. 427-440 (2007).
Warf et al., "MBNL binds similar RNA structures in the CUG repeats of myotonic dystrophy and its pre-mRNA substrate cardiac troponin T," RNA, vol. 13, pp. 2238-2251 (2007).
Weisbart et al., "A Conserved Anti-DNA Antibody Idiotype associated with nephritis in Murine and Human Systemic Lupus Erythematosus," Journal of Immunology, vol. 144(7), pp. 2653-2658 (1990).
Weisbart, R., et al., "An Autoantibody is Modified for Use as a Delivery System to Target the Cell Nucleus: Therapeutic Implications," Journal of Autoimmunity, 11:539-546 (1998).
Weisbart et al., "Cell type specific targeted intracellular delivery into muscle of a monoclonal antibody that binds myosin IIb," Molecular Immunology vol. 39, pp. 783-789 (2003).
Weisbart, R., et al., "An Intracellular Delivery Vehicle for Protein Transduction of Micro-Dystrophin," Journal of Drug Targeting, 13(2):81-87 (2005).
Weisbart, R., et al., Novel Protein Transfection of Primary Rat Cortical Neurons Using an Antibody that Penetrate Living Cells, Journal of Immunology, 164(11):6020-2026 (2000).
Weisbart, R., et al., "Nuclear Delivery of p53 C-terminal Peptides into Cancer Cells Using scFv Fragments of a Monoclonal Antibody that Penetrates Living Cells," Cancer Letters, 195:211-219 (2003).
Wheeler et al., "Reversal of RNA dominance by displacement of protein sequestered on triplet repeat RNA," Science, vol. 325, pp. 336-339 (2009).
Written Opinion of the International Searching Authority (PCT/US2009/005716) dated Dec. 9, 2009.
Yuan et al., "Muscleblind-like 1 interacts with RNA hairpins in splicing target and pathogenic RNAs," Nucleic Acids Research, vol. 35(16), pp. 5474-5486 (2007).
Zack et al., "Mechanisms of Cellular Penetration and Nuclear Localization of an Anti-Double Strand DNA Autoantibody," Journal of Immunology, 157(5):2082-2088 (1996).

METHODS AND COMPOSITIONS FOR TREATMENT OF MYOTONIC DYSTROPHY

RELATED APPLICATIONS

This application is a continuation of U.S. application Ser. No. 12/589,118, filed Oct. 15, 2009, which claims the benefit of priority to U.S. provisional application No. 61/196,142, filed Oct. 15, 2008. The specifications of each of the foregoing applications are hereby incorporated by reference in their entirety.

SEQUENCE LISTING

The instant application contains a Sequence Listing which has been submitted via EFS-Web and is hereby incorporated by reference in its entirety. Said ASCII copy, created on Dec. 9, 2013, is named 1061990002102_Seq.txt, and is 36,942 bytes in size.

BACKGROUND OF THE INVENTION

Myotonic dystrophy (DM or Steinert's disease) is a multisystemic, dominantly inherited disorder often characterized by myotonia or delayed muscle relaxation due to repetitive action potentials in myofibers, and muscle degeneration. Manifestations of DM may also include heart block, ocular cataracts, hypogonadism, and nervous system dysfunction. For example, DM patients often suffer from cardiac conduction defects, smooth muscle involvement, hypersomnia, cataracts, abnormal glucose response, and, in males, premature balding and testicular atrophy. Myotonic dystrophy is the most common muscular dystrophy of adults for which there are no effective therapies. It is a goal of the present disclosure to provide agents and therapeutic treatments for treating myotonic dystrophy.

SUMMARY OF THE INVENTION

The present disclosure provides methods and compositions for delivering a chimeric polypeptide to a muscle cell.

In a first aspect, the disclosure provides chimeric polypeptides comprising an MBNL portion and a targeting moiety. For example, the MBNL portion comprises an MBNL polypeptide and the targeting moiety portion comprises a targeting moiety which targets muscle cells. In certain embodiments, the MBNL polypeptide is selected from an MBNL1 polypeptide, an MBNL2 polypeptide, an MBNL3 polypeptide, or a functional fragment of any of the foregoing.

In certain embodiments, the chimeric polypeptide can bind to CUG repeats. For example, the chimeric polypeptide retains the ability of a native MBNL polypeptide to bind to CUG repeats.

In certain embodiments, the targeting moiety promotes transport of said chimeric polypeptide into said muscle cells. In other words, the chimeric polypeptide can cross cellular membranes and be delivered to muscle cells.

In certain embodiments, the MBNL polypeptide is an MBNL1 polypeptide or a functional fragment thereof. In certain embodiments, the MBNL1 polypeptide comprises an amino acid sequence at least 85%, 90%, 92%, 93%, 95%, 96%, 98%, 99%, or 100% identical to any of SEQ ID NOs: 1-7, or a functional fragment thereof. In certain embodiments, a chimeric polypeptide that include the MBNL1 polypeptide or functional fragment thereof can bind to CUG repeats.

In certain embodiments, the MBNL polypeptide is an MBNL2 polypeptide or a functional fragment thereof. In certain embodiments, the MBNL2 polypeptide comprises an amino acid sequence at least 85%, 90%, 92%, 93%, 95%, 96%, 98%, 99%, or 100% identical to any of SEQ ID NOs: 8 or 9, or a functional fragment thereof. In certain embodiments, a chimeric polypeptide that include the MBNL2 polypeptide or functional fragment thereof can bind to CUG repeats.

In certain embodiments, the MBNL polypeptide is an MBNL3 polypeptide or a functional fragment thereof. In certain embodiments, the MBNL3 polypeptide comprises an amino acid sequence at least 85%, 90%, 92%, 93%, 95%, 96%, 98%, 99%, or 100% identical to any of SEQ ID NOs: 10 or 11, or a functional fragment thereof. In certain embodiments, a chimeric polypeptide that include the MBNL3 polypeptide or functional fragment thereof can bind to CUG repeats.

In certain embodiments, the functional fragment lack a portion of the C-terminus of the native MBNL polypeptide. In certain embodiments, the functional fragment comprises four zinc finger motifs. The chimeric polypeptide of claim 4, wherein the functional fragment of the MBNL1 polypeptide lacks a portion of the C-terminus.

In certain embodiments, the chimeric polypeptide further comprises one or more polypeptide portions that enhance one or more of in vivo stability, in vivo half life, uptake/administration, or purification.

In certain embodiments, the targeting moiety comprises an antibody or an antigen binding fragment thereof. In certain embodiments, the antibody is a monoclonal antibody. In certain embodiments, the antibody is a humanized antibody or a human antibody. In certain embodiments, the targeting moiety comprises a homing peptide which targets muscle cells. In certain embodiments, the targeting moiety targets muscle cells and/or promotes transit across cellular membranes. In certain embodiments, the targeting moiety transits cellular membranes via an equilibrative nucleoside transporter 2 (ENT2) transporter.

In certain embodiments, the antibody is monoclonal antibody 3E10, or an antigen-binding fragment thereof. In certain embodiments, the antibody or antigen binding fragment thereof is an antibody that binds to the same epitope as 3E10, or an antibody that has substantially the same cell penetrating activity as 3E10, or an antigen binding fragment thereof. In certain embodiments, the antibody or antigen-binding fragment thereof is monoclonal antibody 3E10, or a variant thereof that retains the cell penetrating activity of 3E10, or an antigen binding fragment of 3E10 or said 3E10 variant. When reference is made to an antibody, such as 3E10, it should be understood that the antibody can be made by any means. For example, 3E10 refers to an antibody having the amino acid sequence of 3E10—regardless of how the antibody was made.

In certain embodiments, the chimeric polypeptide is produced by chemically conjugating MBNL polypeptide to the targeting moiety. In certain embodiments, the chimeric polypeptide is produced by a recombinant vector encoding both the MBNL polypeptide and the targeting moiety. In certain embodiments, the chimeric polypeptide is produced recombinantly to recombinantly conjugate the MBNL polypeptide to the targeting moiety. Regardless of the method of linking the MBNL portion and the targeting portion, the chimeric polypeptide may optionally include a linker, for example a cleavage linker, between the MBNL portion and the targeting portion. Further, the chimeric polypeptide may be linked via the N-terminus, C-terminus, or an internal amino acid residue of the MBNL portion. Exemplary chimeric polypeptides retain the ability to (i) bind to CUG repeats and (ii) transit a cellular membrane.

In certain embodiments, the chimeric polypeptide is produced in a prokaryotic or eukaryotic cell. In certain embodiments, eukaryotic cell is selected from a yeast cell, an avian cell, an insect cell, or a mammalian cell. In certain embodiments, the prokaryotic cell is a bacterial cell.

In another aspect, the disclosure provides a nucleic acid construct comprising a nucleotide sequence that encodes a chimeric polypeptide. By way of example, the disclosure provides a nucleic acid construct comprising a nucleotide sequence that encodes an MBNL polypeptide, operably linked to a nucleotide sequence that encodes a targeting moiety, wherein the nucleic acid construct encodes a chimeric polypeptide having MBNL biological activity and having the targeting activity of the targeting moiety. In certain embodiments, the nucleic acid construct further comprises a nucleotide sequence that encodes a linker.

In certain embodiments, the targeting moiety targets muscle cells to promote transport into muscle cells. In certain embodiments, the targeting moiety transits cellular membranes via an ENT2 transporter. In certain embodiments, the chimeric polypeptide encoded by the nucleic acid construct binds to CUG repeats.

In certain embodiments, the nucleotide sequence that encodes an MBNL polypeptide encodes an MBNL1 polypeptide or functional fragment thereof. In certain embodiments, the MBNL1 polypeptide comprises an amino acid sequence at least 85%, 90%, 92%, 93%, 95%, 96%, 98%, 99%, or 100% identical to any of SEQ ID NOs: 1-7, or a functional fragment thereof. In certain embodiments, a chimeric polypeptide that include the MBNL1 polypeptide or functional fragment thereof can bind to CUG repeats.

In certain embodiments, the he nucleotide sequence that encodes an MBNL polypeptide encodes an MBNL2 polypeptide or functional fragment thereof. In certain embodiments, the MBNL2 polypeptide comprises an amino acid sequence at least 85%, 90%, 92%, 93%, 95%, 96%, 98%, 99%, or 100% identical to any of SEQ ID NOs: 8 or 9, or a functional fragment thereof. In certain embodiments, a chimeric polypeptide that include the MBNL2 polypeptide or functional fragment thereof can bind to CUG repeats.

The nucleotide sequence that encodes an MBNL polypeptide encodes an MBNL3 polypeptide or functional fragment thereof. In certain embodiments, the MBNL1 polypeptide comprises an amino acid sequence at least 85%, 90%, 92%, 93%, 95%, 96%, 98%, 99%, or 100% identical to any of SEQ ID NOs: 10 or 11, or a functional fragment thereof. In certain embodiments, a chimeric polypeptide that include the MBNL3 polypeptide or functional fragment thereof can bind to CUG repeats.

In certain embodiments, the targeting moiety is an antibody or an antigen binding fragment thereof. In certain embodiments, the antibody or antigen-binding fragment thereof is monoclonal antibody 3E10, or a variant thereof that retains the cell penetrating activity of 3E10, or an antigen binding fragment of 3E10 or said 3E10 variant. In certain embodiments, the antibody or antigen-binding fragment thereof is an antibody that binds to the same epitope as 3E10, or an antibody that has substantially the same cell penetrating activity as 3E10, or an antigen binding fragment thereof. In certain embodiments, the targeting moiety is a homing peptide which targets muscle cells.

In another aspect, the disclosure provides a composition comprising any of the chimeric polypeptides described herein (e.g., chimeric polypeptides comprising an MBNL portion and a targeting moiety portion), including any combination of aspects and embodiments of the invention detailed above or below, and a pharmaceutically acceptable carrier.

In another aspect, the disclosure provides a method of treating myotonic dystrophy in a subject in need thereof. The method comprises administering to the subject a therapeutically effective amount of a chimeric polypeptide comprising: (i) an MBNL polypeptide and (ii) a targeting moiety which targets muscle cells. In certain embodiments, the said MBNL polypeptide is selected from an MBNL1 polypeptide, an MBNL2 polypeptide, an MBNL3 polypeptide, or a functional fragment of any of the foregoing. In certain embodiments, the targeting moiety is selected from an antibody or antigen binding fragment thereof or a homing peptide.

In certain embodiments, the myotonic dystrophy is myotonic dystrophy type I (DM1). In certain embodiments, the myotonic dystrophy is myotonic dystrophy type II (DM2). In certain embodiments, cells of the subject exhibit aberrant microsatellite expansion.

In another aspect, the disclosure provides a method of treating a condition associated with aberrant microsatellite expansion. The method comprises administering to a subject in need thereof, a therapeutically effective amount of a chimeric polypeptide comprising (i) an MBNL polypeptide and (ii) a targeting moiety which targets muscle cells. In certain embodiments, the MBNL polypeptide is selected from an MBNL1 polypeptide, an MBNL2 polypeptide, an MBNL3 polypeptide, or a bioactive fragment of any of the foregoing.

In one embodiment, the condition is myotonic dystrophy. In another embodiment, the condition is caused by mis-splicing of a gene selected from the group consisting of: the Clcn1 skeletal muscle chloride channel, the Amyloid beta (A4) precursor protein (APP), the NMDA receptor NR1 (GRIN1), the Microtubule-associated protein tau (MAPT), and the TNNT2 (cTNT) protein.

In another aspect, the disclosure provides a method of delivering a chimeric polypeptide into a cell via an equilibrative nucleoside transporter (ENT2) pathway. The method comprises contacting a cell with a chimeric polypeptide, which chimeric polypeptide comprises an (i) MBNL polypeptide and (ii) a targeting moiety which mediates transport across a cellular membrane via an ENT2 pathway, thereby delivering the chimeric polypeptide into the cell. In certain embodiments, the cell is a muscle cell.

In another aspect, the disclosure provides a method of delivering a chimeric polypeptide into a muscle cell, comprising contacting a muscle cell with a chimeric polypeptide, which chimeric polypeptide comprises (i) an MBNL polypeptide and (ii) a targeting moiety which promotes transport into muscle cells, thereby delivering the chimeric polypeptide into the muscle cell.

In another aspect, the disclosure provides a method of delivering a chimeric polypeptide to a subject in need thereof, comprising administering to a subject in need thereof a chimeric polypeptide, which chimeric polypeptide comprises (i) an MBNL polypeptide and (ii) a targeting moiety which promotes transport into muscle cells, thereby delivering the chimeric polypeptide into the muscle cell.

In another aspect, the disclosure provides a method of increasing MBNL bioactivity in a muscle cell, comprising contacting a muscle cell with a chimeric polypeptide, which chimeric polypeptide comprises (i) an MBNL polypeptide and (ii) a targeting moiety which promotes transport into muscle cells, thereby increasing MBNL bioactivity in the muscle cell. In certain embodiments, the targeting moiety promotes transport via an ENT2 transporter.

In another aspect, the disclosure provides use of any of the chimeric polypeptides described herein (e.g., chimeric polypeptides comprising an MBNL portion and a targeting moiety portion—including any combination of aspects and embodiments of the invention detailed above or below) in the manufacture of a medicament for treating myotonic dystrophy.

In another aspect, the disclosure provides use of any of the chimeric polypeptides described herein (e.g., chimeric polypeptides comprising an MBNL portion and a targeting moiety portion—including any combination of aspects and embodiments of the invention detailed above or below) for treating myotonic dystrophy.

In another aspect, the disclosure provides use of any of the chimeric polypeptides described herein (e.g., chimeric polypeptides comprising an MBNL portion and a targeting moiety portion—including any combination of aspects and embodiments of the invention detailed above or below) to deliver said chimeric polypeptide into muscle cells.

In another aspect, the disclosure provides use of any of the chimeric polypeptides described herein (e.g., chimeric polypeptides comprising an MBNL portion and a targeting moiety portion—including any combination of aspects and embodiments of the invention detailed above or below) in the manufacture of a medicament for delivery into muscle cells.

For any of the foregoing aspects of the invention, the invention contemplates any of the embodiments set forth above or below. Also including are combinations of any of the aspects and embodiments set forth above or below.

In certain embodiments, the disclosure provides a chimeric polypeptide comprising: (i) an MBNL polypeptide selected from the group consisting of an MBNL1 polypeptide, an MBNL2 polypeptide, and an MBNL3 polypeptide; and (ii) a targeting moiety which targets muscle cells. To illustrate, the MBNL1 polypeptide comprises an amino acid sequence at least 90% identical to any of SEQ ID NOs: 1-7, or functional fragments thereof, the MBNL2 polypeptide comprises an amino acid sequence at least 90% identical to any of SEQ ID NOs: 8-9, or functional fragments thereof, and the MBNL3 polypeptide comprises an amino acid sequence at least 90% identical to any of SEQ ID NOs: 10-11, or functional fragments thereof. Optionally, the chimeric polypeptide comprises a functional fragment of the MBNL1 polypeptide which lacks a portion of the C-terminus. Optionally, the chimeric polypeptide comprises a functional fragment of the MBNL1 polypeptide which comprise all four zinc finger motifs. In certain embodiments, the MBNL polypeptide of functional fragment is from an approximately 40 kD MBNL polypeptide. In certain embodiments, the functional fragment comprises approximately amino acids 1-260 of an MBNL polypeptide. In certain embodiments, the functional fragment is at least about 200, 210, 220, 225, 230, 240, 250, or at least about 260 amino acid residues of an MBNL polypeptide. Optionally, the MBNL polypeptide within the chimeric polypeptide further comprises one or more polypeptide portions that enhance one or more of in vivo stability, in vivo half life, uptake/administration, and/or purification.

In certain embodiments, the targeting moiety of the subject chimeric polypeptide comprises an antibody (e.g., a monoclonal antibody or fragments thereof). In certain specific embodiments, the targeting moiety is the monoclonal antibody 3E10 or an scFv fragment thereof. In other embodiments, the targeting moiety of the subject chimeric polypeptide comprises a homing peptide which targets muscle cells. In certain aspects, the chimeric polypeptide is produced by chemically conjugating MBNL polypeptide to the targeting moiety. In certain embodiments, the chimeric polypeptide may be produced recombinantly to recombinantly conjugate the MBNL polypeptide, or bioactive fragment thereof, to the targeting moiety. For example, the chimeric polypeptide may be produced by a recombinant vector encoding both the MBNL polypeptide and the targeting moiety.

In certain embodiments, the disclosure provides a pharmaceutical composition comprising the subject chimeric polypeptide as described above, and a pharmaceutically acceptable carrier. Optionally, the pharmaceutical composition may further comprise a second agent which acts in an additive or synergistic manner for treating myotonic dystrophy. For example, the second agent in the combination therapy is selected from a small molecule, a polypeptide, an antibody, an antisense oligonucleotide, and an siRNA molecule. In some embodiments, the second therapy may be a drug for helping to relieve one or more symptoms of myotonic dystrophy, or a physical or other non-drug therapy for treating or otherwise helping to relieve one or more symptoms of myotonic dystrophy. Exemplary non-drug therapies include, but are not limited to, ventilatory therapy, occupational therapy, acupuncture, and massage.

In certain embodiments, the disclosure provides a method of treating myotonic dystrophy in a subject in need thereof. Such method comprises administering to the subject a therapeutically effective amount of a chimeric polypeptide comprising: (i) an MBNL polypeptide selected from the group consisting of an MBNL1 polypeptide, an MBNL2 polypeptide, and an MBNL3 polypeptide; and (ii) a targeting moiety which targets muscle cells. The myotonic dystrophy may be myotonic dystrophy type I (DM1) or myotonic dystrophy type II (DM2). Optionally, cells of the subject exhibit aberrant microsatellite expansion. Preferably, the subject is a human. To illustrate, the MBNL1 polypeptide comprises an amino acid sequence at least 90% identical to any of SEQ ID NOs: 1-7, or functional fragments thereof, the MBNL2 polypeptide comprises an amino acid sequence at least 90% identical to any of SEQ ID NOs: 8-9, or functional fragments thereof, and the MBNL3 polypeptide comprises an amino acid sequence at least 90% identical to any of SEQ ID NOs: 10-11, or functional fragments thereof. Optionally, the chimeric polypeptide comprises a functional fragment of the MBNL1 polypeptide which lacks a portion of the C-terminus. Optionally, the chimeric polypeptide comprises a functional fragment of the MBNL1 polypeptide which comprise all four zinc finger motifs. Optionally, the MBNL polypeptide within the chimeric polypeptide further comprises one or more polypeptide portions that enhance one or more of in vivo stability, in vivo half life, uptake/administration, and/or purification. In certain embodiments, the targeting moiety comprises an antibody (e.g., a monoclonal antibody or fragments thereof). In certain specific embodiments, the targeting moiety is the monoclonal antibody 3E10 or an scFv fragment thereof. For example, the antibody or antigen-binding fragment thereof may be monoclonal antibody 3E10, or a variant thereof that retains the cell penetrating activity of 3E10, or an antigen binding fragment of 3E10 or said 3E10 variant. In other embodiments, the targeting moiety comprises a homing peptide which targets muscle cells. Preferably, the chimeric polypeptide is formulated with a pharmaceutically acceptable carrier. Optionally, the method further comprises administering to the subject a second agent which acts in an additive or synergistic manner for treating myotonic dystrophy. The chimeric polypeptide may be administered systemically or locally. In certain specific embodiments, the chimeric polypeptide is administered to the subject intravenously.

In certain embodiments, the disclosure provides a method of treating a condition or disease associated with aberrant microsatellite expansion. Such method comprises administering to a subject in need thereof, a therapeutically effective amount of a chimeric polypeptide comprising: (i) an MBNL polypeptide selected from the group consisting of an MBNL1 polypeptide, an MBNL2 polypeptide, and an MBNL3 polypeptide; and (ii) a targeting moiety which targets muscle cells. For example, the condition or disease is myotonic dystrophy. In certain embodiments, the condition or disease is caused by mis-splicing of a gene selected from the group consisting of: the Clcn1 skeletal muscle chloride channel, the Amyloid beta (A4) precursor protein (APP), the NMDA receptor NR1 (GRIN1), the Microtubule-associated protein tau (MAPT), and the TNNT2 (cTNT) protein.

In certain embodiments, the MBNL polypeptide is selected from an MBNL1 polypeptide, an MBNL2 polypeptide, an MBNL3 polypeptide, or a functional fragment of any of the foregoing.

In certain embodiments, the chimeric polypeptide can bind to CUG repeats. For example, the chimeric polypeptide retains the ability of a native MBNL polypeptide to bind to CUG repeats.

In certain embodiments, the targeting moiety promotes transport of said chimeric polypeptide into said muscle cells. In other words, the chimeric polypeptide can cross cellular membranes and be delivered to muscle cells.

In certain embodiments, the MBNL polypeptide is an MBNL1 polypeptide or a functional fragment thereof. In certain embodiments, the MBNL1 polypeptide comprises an amino acid sequence at least 85%, 90%, 92%, 93%, 95%, 96%, 98%, 99%, or 100% identical to any of SEQ ID NOs: 1-7, or a functional fragment thereof. In certain embodiments, a chimeric polypeptide that include the MBNL1 polypeptide or functional fragment thereof can bind to CUG repeats.

In certain embodiments, the MBNL polypeptide is an MBNL2 polypeptide or a functional fragment thereof. In certain embodiments, the MBNL2 polypeptide comprises an amino acid sequence at least 85%, 90%, 92%, 93%, 95%, 96%, 98%, 99%, or 100% identical to any of SEQ ID NOs: 8 or 9, or a functional fragment thereof. In certain embodiments, a chimeric polypeptide that include the MBNL2 polypeptide or functional fragment thereof can bind to CUG repeats.

In certain embodiments, the MBNL polypeptide is an MBNL3 polypeptide or a functional fragment thereof. In certain embodiments, the MBNL3 polypeptide comprises an amino acid sequence at least 85%, 90%, 92%, 93%, 95%, 96%, 98%, 99%, or 100% identical to any of SEQ ID NOs: 10 or 11, or a functional fragment thereof. In certain embodiments, a chimeric polypeptide that include the MBNL3 polypeptide or functional fragment thereof can bind to CUG repeats.

In certain embodiments, the functional fragment lack a portion of the C-terminus of the native MBNL polypeptide. In certain embodiments, the functional fragment comprises four zinc finger motifs. The chimeric polypeptide of claim 4, wherein the functional fragment of the MBNL1 polypeptide lacks a portion of the C-terminus.

In certain embodiments, the chimeric polypeptide further comprises one or more polypeptide portions that enhance one or more of in vivo stability, in vivo half life, uptake/administration, or purification.

In certain embodiments, the targeting moiety comprises an antibody or an antigen binding fragment thereof. In certain embodiments, the antibody is a monoclonal antibody. In certain embodiments, the antibody is a humanized antibody or a human antibody. In certain embodiments, the targeting moiety comprises a homing peptide which targets muscle cells. In certain embodiments, the targeting moiety targets muscle cells and/or promote transit across cellular membranes. In certain embodiments, the targeting moiety transits cellular membranes via an equilibrative nucleoside transporter 2 (ENT2) transporter.

In certain embodiments, the antibody is monoclonal antibody 3E10, or an antigen-binding fragment thereof. In certain embodiments, the antibody or antigen binding fragment thereof is an antibody that binds to the same epitope as 3E10, or an antibody that has substantially the same cell penetrating activity as 3E10, or an antigen binding fragment thereof. In certain embodiments, the antibody or antigen-binding fragment thereof is monoclonal antibody 3E10, or a variant thereof that retains the cell penetrating activity of 3E10, or an antigen binding fragment of 3E10 or said 3E10 variant. When reference is made to an antibody, such as 3E10, it should be understood that the antibody can be made by any means. For example, 3E10 refers to an antibody having the amino acid sequence of 3E10—regardless of how the antibody was made.

In certain embodiments, the chimeric polypeptide is produced by chemically conjugating MBNL polypeptide to the targeting moiety. In certain embodiments, the chimeric polypeptide is produced by a recombinant vector encoding both the MBNL polypeptide and the targeting moiety. In certain embodiments, the chimeric polypeptide is produced recombinantly to recombinantly conjugate the MBNL polypeptide to the targeting moiety. Regardless of the method of linking the MBNL portion and the targeting portion, the chimeric polypeptide may optionally include a linker, for example a cleavage linker, between the MBNL portion and the targeting portion. Further, the chimeric polypeptide may be linked via the N-terminus, C-terminus, or an internal amino acid residue of the MBNL portion. Exemplary chimeric polypeptides retain the ability to (i) bind to CUG repeats and (ii) transit a cellular membrane.

In certain embodiments, the chimeric polypeptide is produced in a prokaryotic or eukaryotic cell. In certain embodiments, eukaryotic cell is selected from a yeast cell, an avian cell, an insect cell, or a mammalian cell. In certain embodiments, the prokaryotic cell is a bacterial cell.

In certain embodiments, the chimeric polypeptide retains a biological function of the native MBNL polypeptide. In certain embodiments, the targeting moiety promotes transport of the chimeric polypeptide across a cellular membrane (e.g., promotes delivery of the chimeric polypeptide into the cell).

In certain embodiments, the chimeric polypeptide is delivered to a human cell and/or a human patient. In certain embodiments, the chimeric polypeptide is delivered to a non-human cell and/or a non-human patient. In certain embodiments, a biological activity of a chimeric polypeptide is evaluated in vitro. In certain embodiments, a biological activity of a chimeric polypeptide is evaluated in vivo.

The invention contemplates all combinations of any of the foregoing aspects and embodiments, as well as combinations with any of the embodiments set forth in the detailed description and examples.

DETAILED DESCRIPTION OF THE INVENTION

Proteins in the muscleblind-like (MBNL) family bind to expanded CUG repeats in vitro and colocalize with mutant DM and $HSA^{LR}$ transcripts in vivo. Human muscleblind genes MBNL1, MBNL2, and MBNL3 are homologous to the *Drosophila* gene muscleblind, which is essential for muscle and eye differentiation. MBNL1, the major MBNL gene expressed in human skeletal muscle, encodes multiple protein isoforms (e.g., SEQ ID NOs: 1-7), including some that bind to expanded CUG repeats (41 to 42 kD) and others that fail to bind (31 kD isoform), generated by exon 3 skipping. MBNL1 was identified in HeLa cells based on its ability to bind double-stranded CUG repeats (Miller et al., 2000, EMBO J 19: 4439-4448). All three MBNL gene products colocalize with the expanded repeat RNA foci in vivo (Fardaei et al., 2002, Hum Mol Genet. 11: 805-814). Loss of MBNL function due to sequestration on CUG repeat RNA is proposed to play a role in DM pathogenesis (Miller et al., 2000, EMBO J 19: 4439-4448). While expression of CUG and CCUG expansion RNAs induces MBNL recruitment into nuclear RNA foci, there is no evidence that this relocalization results in muscleblind depletion and functional impairment.

In certain aspects, the disclosure provides numerous muscleblind-like (MBNL) polypeptides that may be used to treat conditions associated with aberrant microsatellite expansion such as myotonic dystrophy. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

In certain embodiments, the invention provides a chimeric polypeptide comprising (i) an MBNL polypeptide (e.g., an MBNL1 polypeptide, an MBNL2 polypeptide, or an MBNL3 polypeptide, or a functional fragment thereof); and (ii) a targeting moiety which targets muscle cells.

I. MBNL Polypeptides

As used herein, the MBNL polypeptides include various splicing isoforms, functional fragments and variants, fusion proteins, and modified forms of the wildtype MBNL polypeptide (e.g., MBNL1, MBNL2, or MBNL3). Such isoforms, functional fragments or variants, fusion proteins, and modified forms of the MBNL polypeptides have at least a portion of the amino acid sequence of substantial sequence identity to the native MBNL protein, and retain at least one function of the native MBNL protein. In certain embodiments, a functional fragment, variant, or fusion protein of an MBNL polypeptide comprises an amino acid sequence that is at least 80%, 85%, 90%, 95%, 97%, 98%, 99% or 100% identical to any of MBNL1 polypeptides (e.g., SEQ ID NOs: 1-7), MBNL2 polypeptides (e.g., SEQ ID NOs: 8-9), or MBNL3 polypeptides (e.g., SEQ ID NOs: 10-11).

In certain specific embodiments, the chimeric polypeptide comprises a functional fragment of the MBNL1 polypeptide which lacks a portion of the C-terminus. Optionally, the chimeric polypeptide comprises a functional fragment of the MBNL1 polypeptide which comprise all four zinc finger motifs. The structure and various motifs of the MBNL1 polypeptide are known in the art (see, e.g., Kino et al., 2004, Human Molecular Genetics, 13:495-507). An exemplary functional fragment of the MBNL1 polypeptide comprises residues 1-248 of SEQ ID NO: 3, lacking the 121 residues of the C-terminus. Optionally, functional fragments of the MBNL1 polypeptide may comprise residues 1-250, 1-260, 1-270, 1-280, 1-290, 1-300, 1-310, 10-320, 1-330, 1-340, 1-350, or 1-360 of SEQ ID NO: 3. In certain embodiments, similar functional fragments from other MBNL polypeptides can be used. In certain embodiments, similar functional fragments from other MBNL polypeptides whose molecular weight is about 40 kD can be used.

In certain embodiments, fragments or variants of the MBNL polypeptides can be obtained by screening polypeptides recombinantly produced from the corresponding fragment of the nucleic acid encoding an MBNL polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native MBNL protein, for example, by testing their ability to treat myotonic dystrophy.

In certain embodiments, the present invention contemplates modifying the structure of an MBNL polypeptide for such purposes as enhancing therapeutic or prophylactic efficacy, or stability (e.g., ex vivo shelf life and resistance to proteolytic degradation in vivo). Such modified MBNL polypeptides are considered functional equivalents of the naturally-occurring MBNL polypeptide. Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the MBNL biological activity of the resulting molecule. Conservative replacements are those that take place within a family of amino acids that are related in their side chains.

This invention further contemplates generating sets of combinatorial mutants of an MBNL polypeptide, as well as truncation mutants, and is especially useful for identifying functional variant sequences. Combinatorially-derived variants can be generated which have a selective potency relative to a naturally occurring MBNL polypeptide. Likewise, mutagenesis can give rise to variants which have intracellular half-lives dramatically different than the corresponding wildtype MBNL polypeptide. For example, the altered protein can be rendered either more stable or less stable to proteolytic degradation or other cellular process which result in destruction of, or otherwise inactivation of the protein of interest (e.g., MBNL1, MBNL2, or MBNL3). Such variants can be utilized to alter the MBNL polypeptide level by modulating their half-life. There are many ways by which the library of potential MBNL variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, MBNL polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the MBNL polypeptide (e.g., MBNL1, MBNL2, or MBNL3).

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the MBNL polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an MBNL polypeptide may include a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the MBNL polypeptides.

In certain embodiments, an MBNL polypeptide may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified MBNL polypeptides may contain non-amino acid elements, such as lipids, poly- or mono-saccharide, and phosphates. Effects of such non-amino acid elements on the functionality of an MBNL polypeptide may be tested for its biological activity, for example, its ability to treat myotonic dystrophy. In certain embodiments, the MBNL polypeptide may further comprise one or more polypeptide portions that enhance one or more of in vivo stability, in vivo half life, uptake/administration, and/or purification. In other embodiments, the targeting moiety comprises an antibody or an antigen-binding fragment thereof.

In one specific embodiment of the present invention, an MBNL polypeptide may be modified with nonproteinaceous polymers. In one specific embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the MBNL protein to carry out the functions associated with wildtype MBNL proteins, for example, the regulation of exon splicing events in a cell or the ability to bind CUG repeats (for example, double stranded CUG repeats). The terms "biological activity", "bioactivity", and "functional" are used interchangeably herein. In certain embodiments, and as described herein, an MBNL protein or chimeric polypeptide having biological activity has the ability to bind CUG repeats (Warf, 2007, RNA, 12: 2238-51). In other embodiments, an MBNL protein or chimeric polypeptide having biological activity has the ability to bind CAG repeats (Ho, 2005, J. Cell Science, 118: 2923-2933). In other embodiments, an MBNL protein or chimeric polypeptide having biological activity has the ability to bind one or more of CUG repears, CAG repeats, CCUG, CCG or CGG repeats. In certain embodiments, an MBNL having biological activity has the ability to bind to CAG, CCUG and CUG repeats. As used herein, "fragments" are understood to include bioactive fragments (also referred to as functional fragments) or bioactive variants that exhibit "bioactivity" as described herein. That is, bioactive fragments or variants of MBNL exhibit bioactivity that can be measured and tested. For example, bioactive fragments/functional fragments or variants exhibit the same or substantially the same bioactivity as native (i.e., wild-type, or normal) MBNL protein, and such bioactivity can be assessed by the ability of the fragment or variant to, e.g., remove fetal exons from DM1 myoblasts; bind to CUG repeats (as evaluated in vitro or in vivo). As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the MBNL polypeptide will preferably retain at least 50%, 60%, 70%, 80%, 85%, 90%, 95% or 100% of the MBNL biological activity associated with the native MBNL polypeptide. In certain embodiments, fragments or variants of the MBNL polypeptide have a half-life ($t_{1/2}$) which is enhanced relative to the half-life of the native protein. Preferably, the half-life of MBNL fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native MBNL protein. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native MBNL protein.

With respect to methods of increasing MBNL bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing chimeric polypeptides as described herein. Further, the present disclosure contemplates any number of combinations of the foregoing methods and compositions.

In certain aspects, an MBNL polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the MBNL polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

In some embodiments, an MBNL protein may be a fusion protein with an Fc region of an immunoglobulin. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM. Furthermore, it is contemplated that substitution or deletion of amino acids within the immunoglobulin heavy chain constant regions may be useful in the practice of the invention. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In certain embodiments of any of the foregoing, the MBNL portion of the chimeric protein comprises MBNL1, or a functional fragment thereof. In certain embodiments, such MBNL1 polypeptide or functional fragment thereof retains the ability of native MBNL1 to bind to CUG repeats, as evaluated in vitro or in vivo. Further, in certain embodiments, the chimeric polypeptide that comprises such an MBNL1 polypeptide or functional fragment thereof can bind to CUG repeats. Exemplary functional fragments comprise at least 50, at least 60, at least 75, at least 100, at least 125, at least 150, at least 175, at least 200, at least 225, at least 230, at least 250, at least 260, at least 275, or at least 300 consecutive amino acid residues of a full length MBNL1 polypeptide. Similarly, in certain embodiments, the invention contemplates chimeric proteins where the MBNL portion is a variant of any of the foregoing MBNL1 polypeptides or bioactive fragments. Exemplary variants have an amino acid sequence at least 90%, 92%, 95%, 96%, 97%, 98%, or at least 99% identical to the amino acid sequence of a native MBNL1 polypeptide or functional fragment thereof, and such variants retain the ability to bind to CUG repeats, as evaluated in vitro or in vivo. The invention contemplates chimeric proteins and the use of such proteins wherein the MBNL portion comprises any of the MBNL1 polypeptides, fragments, or variants described herein in combination with any targeting moiety described herein. Exemplary MBNL1 polypeptides are set forth in SEQ ID NOs: 1-7. Moreover, in certain embodiments, the MBNL portion of any of the foregoing chimeric polypeptides may, in certain embodiments, by a fusion protein.

In certain embodiments of any of the foregoing, the MBNL portion of the chimeric protein comprises MBNL2, or a functional fragment thereof. In certain embodiments, such MBNL2 polypeptide or functional fragment thereof retains the ability of to bind to CUG repeats, as evaluated in vitro or in vivo. Further, in certain embodiments, the chimeric polypeptide that comprises such an MBNL2 polypeptide or functional fragment thereof can bind to CUG repeats. Exemplary bioactive fragments comprise at least 50, at least 60, at least 75, at least 100, at least 125, at least 150, at least 175, at least 200, at least 225, at least 230, at least 250, at least 260, at least 275, or at least 300 consecutive amino acid residues of a full length MBNL2 polypeptide. Similarly, in certain embodiments, the invention contemplates chimeric proteins where the MBNL portion is a variant of any of the foregoing MBNL2 polypeptides or functional fragments. Exemplary variants have an amino acid sequence at least 90%, 92%, 95%, 96%, 97%, 98%, or at least 99% identical to the amino acid sequence of a native MBNL2 polypeptide or bioactive fragment thereof, and such variants retain the ability of native MBNL2 to bind to CUG repeats, as evaluated in vitro or in vivo. The invention contemplates chimeric proteins and the use of such proteins wherein the MBNL portion comprises any of the MBNL2 polypeptides, fragments, or variants described herein in combination with any targeting moiety described herein. Exemplary MBNL2 polypeptides are set forth in SEQ ID NOs: 8-9. Moreover, in certain embodiments, the MBNL portion of any of the foregoing chimeric polypeptides may, in certain embodiments, by a fusion protein.

In certain embodiments of any of the foregoing, the MBNL portion of the chimeric protein comprises MBNL3, or a functional fragment thereof. In certain embodiments, such MBNL3 polypeptide or functional fragment thereof retains the ability of native MBNL3 to bind to CUG repeats, as evaluated in vitro or in vivo. Further, in certain embodiments, the chimeric polypeptide that comprises such an MBNL3 polypeptide or functional fragment thereof can bind to CUG repeats. Exemplary functional fragments comprise at least 50, at least 60, at least 75, at least 100, at least 125, at least 150, at least 175, at least 200, at least 225, at least 230, at least 250, at least 260, at least 275, or at least 300 consecutive amino acid residues of a full length MBNL3 polypeptide. Similarly, in certain embodiments, the invention contemplates chimeric proteins where the MBNL portion is a variant of any of the foregoing MBNL3 polypeptides or functional fragments. Exemplary variants have an amino acid sequence at least 90%, 92%, 95%, 96%, 97%, 98%, or at least 99% identical to the amino acid sequence of a native MBNL3 polypeptide or functional fragment thereof, and such variants retain the ability to bind to CUG repeats, as evaluated in vitro or in vivo. The invention contemplates chimeric proteins and the use of such proteins wherein the MBNL portion comprises any of the MBNL3 polypeptides, fragments, or variants described herein in combination with any targeting moiety described herein. Exemplary MBNL3 polypeptides are set forth in SEQ ID NO: 10-11. Moreover, in certain embodiments, the MBNL portion of any of the foregoing chimeric polypeptides may, in certain embodiments, by a fusion protein.

II. Targeting Moieties

As used herein, the term "targeting moiety" refers to a moiety capable of interacting with a target tissue or a cell type. Preferably, this disclosure relates to a targeting moiety which targets muscle cells. Targeting moieties having limited cross-reactivity are generally preferred. In certain embodiments, suitable targeting moieties include, for example, antibodies, monoclonal antibodies, or derivatives or analogs thereof; and other targeting moieties include for example, homing peptides, fusion proteins, receptors, ligands, aptamers, peptidomimetics, and any member of a specific binding pair. In some embodiments, the targeting moiety helps the chimeric polypeptide effectively and efficiently transit cellular membranes. In some embodiments, the targeting moiety transits cellular membranes via an equilibrative nucleoside transporter 2 (ENT2) transporter. In other words, the targeting moiety may promote transport of the chimeric polypeptide across cellular membranes via an ENT2 transporter. In other embodiments, the targeting moiety targets cells other than muscle cells, e.g., neurons, epithelial cells, liver cells, kidney cells or Leydig cells.

(a) Antibodies

In certain aspects, a targeting moiety may comprise an antibody, including a monoclonal antibody, a polyclonal antibody, and a humanized antibody. Without being bound by theory, such antibody may bind to an antigen of a target tissue and thus mediate the delivery of the subject chimeric polypeptide to the target tissue (e.g., muscle). In some embodiments, targeting moieties may comprise antibody fragments, derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In certain embodiments, the antibodies or variants thereof, may be modified to make them less immunogenic when administered to a subject. For example, if the subject is human, the antibody may be "humanized"; where the complementarity determining region(s) of the hybridoma-derived antibody has been transplanted into a human monoclonal antibody, for example as described in Jones, P. et al. (1986), *Nature,* 321, 522-525 or Tempest et al. (1991), *Biotechnology,* 9, 266-273. In some embodiments, the targeting moiety is any peptide or antibody-like protein having the complementarity determining regions (CDRs) of the 3E10 antibody sequence, or of an antibody that binds the same epitope as 3E10. Also, transgenic mice, or other mammals, may be used to express humanized or human antibodies. Such humanization may be partial or complete.

In certain embodiments, the targeting moiety comprises the monoclonal antibody 3E10 or an antigen binding fragment thereof. For example, the antibody or antigen-binding fragment thereof may be monoclonal antibody 3E10, or a variant thereof that retains the cell penetrating activity of 3E10, or an antigen binding fragment of 3E10 or said 3E10 variant. Additionally, the antibody or antigen-binding fragment thereof may be an antibody that binds to the same epitope as 3E10, or an antibody that has substantially the same cell penetrating activity as 3E10, or an antigen binding fragment thereof. In some embodiments, the targeting moiety may comprise a homing peptide that targets ENT2. In certain embodiments, the antigen binding fragment is an Fv or scFv fragment thereof. Monoclonal antibody 3E10 can be produced by a hybridoma 3E10 placed permanently on deposit with the American Type Culture Collection (ATCC) under ATCC accession number PTA-2439 and is disclosed in U.S. Pat. No. 7,189,396. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used to refer to the antibody, regardless of the method used to produce the antibody. Similarly, when referring to variants or antigen-binding fragments of 3E10, such terms are used without reference to the manner in which the antibody was produced.

The targeting moiety may also include variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, and the like). Such variants include variants wherein one or more conservative substitutions are introduced into the heavy chain, the light chain and/or the constant region(s) of the antibody.

Monoclonal antibody 3E10 has been shown to penetrate cells without toxicity and has attracted considerable interest as a means to deliver proteins and nucleic acids into the cytoplasmic or nuclear spaces of target tissues (Weisbart R H et al., J. Autoimmun. 1998 October; 11(5):539-46; Weisbart R H, et al. Mol. Immunol. 2003 March; 39(13):783-9; Zack D J et al., J. Immunol. 1996 Sep. 1; 157(5):2082-8.). Further, the VH and Vk sequences of 3E10 are highly homologous to human antibodies, with respective humanness z-scores of 0.943 and −0.880. Thus, Fv3E10 is expected to induce less of an anti-antibody response than many other approved humanized antibodies (Abhinandan K R et al., Mol. Biol. 2007 369, 852-862). A single chain Fv fragment of 3E10 possesses all the cell penetrating capabilities of the original monoclonal antibody, and proteins such as catalase, dystrophin, HSP70 and p53 retain their activity following conjugation to Fv3E10 (Hansen J E et al., Brain Res. 2006 May 9; 1088(1):187-96; Weisbart R H et al., Cancer Lett. 2003 Jun. 10; 195(2):211-9; Weisbart R H et al., J Drug Target. 2005 February; 13(2):81-7; Weisbart R H et al., J. Immunol. 2000 Jun. 1; 164(11):6020-6; Hansen J E et al., J Biol. Chem. 2007 Jul. 20; 282(29):20790-3). The 3E10 is built on the antibody scaffold present in all mammals; a mouse variable heavy chain and variable kappa light chain. 3E10 gains entry to cells via the ENT2 nucleotide transporter that is particularly enriched in skeletal muscle and cancer cells, and in vitro studies have shown that 3E10 is nontoxic. (Weisbart R H et al., Mol. Immunol. 2003 March; 39(13):783-9; Pennycooke M et al., Biochem Biophys Res Commun. 2001 Jan. 26; 280(3):951-9). Given the affinity of 3E10 and fragments thereof for skeletal muscle, and the ability of various conjugates of 3E10 and MBNL to maintain their respective activities, a recombinant 3E10-MBNL therapy represents a valuable approach to treat MBNL. As described herein, a recombinant 3E10 can be chemically or genetically conjugated to human MBNL (hMBNL) and the activity of each conjugate may be confirmed in vitro. Further, the purified conjugates may be injected into MBNL deficient mice and improvements in disease phenotype, as described herein, may be examined. The targeting moiety may also include mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain, the light chain and/or the constant region(s) of the antibody. Numerous variants of mAb 3E10 have been characterized in, e.g., U.S. Pat. No. 7,189,396 and WO 2008/091911, the teachings of which are incorporated by reference herein in their entirety. In certain embodiments, the targeting moiety comprises an antibody having an amino acid sequence at least 80%, 85%, 90%, 95%, 96%, 97%, 99%, or 100% identical to the amino acid sequence of 3E10, or at least 80%, 85%, 90%, 95%, 96%, 97%, 99%, or 100% identical to the amino acid sequence of a single chain Fv of 3E10 (for example, a single chain Fv comprising SEQ ID NOs 12 and 14). In certain embodiments, the targeting moiety comprises a single chain Fv of 3E10, and the amino acid sequence of the $V_H$ domain is at least 90%, 95%, 96%, 97%, 98%, 99%, or 100% identical to SEQ ID NO: 12, and amino acid sequence of the $V_L$ domain is at least 90%, 95%, 96%, 97%, 98%, 99%, or 100% identical to SEQ ID NO: 14. The variant 3E10 or fragment thereof retains the function of a targeting moiety.

In other embodiments, the antibodies or fragments thereof target cells other than muscle cells, e.g., neurons, epithelial cells, liver cells, kidney cells or Leydig cells.

Preparation of antibodies or fragments thereof (e.g., an single chain Fv fragment encoded by $V_H$-linker-$V_L$) is well known in the art. In particular, methods of recombinant production of mAb 3E10 antibody fragments as well as conjugates thereof have been described in WO 2008/091911. Further, methods of generating scFv fragments of antibodies are well known in the art. The exemplary method of the present disclosure uses a (GGGGS)3 linker. However, it is understood that other linkers may also be designed. For example, typical surface amino acids in flexible protein regions include Gly, Asn and Ser. Permutations of amino acid sequences containing Gly, Asn and Ser would be expected to satisfy the criteria (e.g., flexible with minimal hydrophobic or charged character) for a linker sequence. Other near neutral amino acids, such as Thr and Ala, can also be used in the linker sequence. In a specific embodiment, a linker sequence length of about 15 amino acids can be used to provide a suitable separation of functional protein domains, although longer or shorter linker sequences may also be used.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W.H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker- V<sub>L</sub> product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13. In certain embodiments, an antibody or antibody fragment is made recombinantly. In other words, once the sequence of the antibody is known (for example, using the methods described above), the antibody can be made recombinantly using standard techniques.

In certain embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

(b) Homing Peptides

In certain aspects, a targeting moiety may comprise a homing peptide which selectively directs the subject chimeric MBNL polypeptide to a target tissue (e.g., muscle). For example, delivering a chimeric polypeptide to the muscle can be mediated by a homing peptide comprising an amino acid sequence of ASSLNIA (SEQ ID NO: 15). Further exemplary homing peptides are disclosed in WO 98/53804. Homing peptides for a target tissue (or organ) can be identified using various methods well known in the art. Additional examples of homing peptides include the HIV transactivator of transcription (TAT) which comprises the nuclear localization sequence Tat48-60; Drosophila antennapedia transcription factor homeodomain (e.g., Penetratin which comprises Antp43-58 homeodomain 3rd helix); Homo-arginine peptides (e.g., Arg7 (SEQ ID NO: 16) peptide-PKC-ε agonist protection of ischemic rat heart); alpha-helical peptides; cationic peptides ("superpositively" charged proteins). In some embodiments, the homing peptide targets ENT2. In other embodiments, the homing peptide targets muscle cells. The muscle cells targeted by the homing peptide may include skeletal, cardiac or smooth muscle cells. In other embodiments, the homing peptide targets neurons, epithelial cells, liver cells, kidney cells or Leydig cells.

Additionally, homing peptides for a target tissue (or organ) can be identified using various methods well known in the art. Once identified, a homing peptide that is selective for a particular target tissue can be used, in certain embodiments.

An exemplary method is the in vivo phage display method. Specifically, random peptide sequences are expressed as fusion peptides with the surface proteins of phage, and this library of random peptides are infused into the systemic circulation. After infusion into host mice, target tissues or organs are harvested, the phage is then isolated and expanded, and the injection procedure repeated two more times. Each round of injection includes, by default, a negative selection component, as the injected virus has the opportunity to either randomly bind to tissues, or to specifically bind to non-target tissues. Virus sequences that specifically bind to non-target tissues will be quickly eliminated by the selection process, while the number of non-specific binding phage diminishes with each round of selection. Many laboratories have identified the homing peptides that are selective for vasculature of brain, kidney, lung, skin, pancreas, intestine, uterus, adrenal gland, retina, muscle, prostate, or tumors. See, for example, Samoylova et al., 1999, *Muscle Nerve,* 22:460; Pasqualini et al., 1996, *Nature,* 380:364; Koivunen et al., 1995, *Biotechnology,* 13:265; Pasqualini et al., 1995, J. Cell Biol., 130: 1189; Pasqualini et al., 1996, *Mole. Psych.,* 1:421, 423; Rajotte et al., 1998, *J. Clin. Invest.,* 102:430; Rajotte et al., 1999, *J. Biol. Chem.,* 274:11593. See, also, U.S. Pat. Nos. 5,622,699; 6,068,829; 6,174,687; 6,180,084; 6,232,287; 6,296,832; 6,303,573; 6,306,365. Homing peptides that target any of the above tissues may be used for targeting an MBNL protein to that tissue.

III. Chimeric Polypeptides

Chimeric polypeptides of the present invention can be made in various manners. In certain embodiments, the C-terminus of an MBNL polypeptide can be linked to the N-terminus of a targeting moiety (e.g., an antibody or a homing peptide). Alternatively, the C-terminus of a targeting moiety (e.g., an antibody or a homing peptide) can be linked to the N-terminus of an MBNL polypeptide. For example, chimeric polypeptides an be designed to place the MBNL polypeptide at the amino or carboxy terminus of either the antibody heavy or light chain of mAb 3E10. In certain embodiments, potential configurations include the use of truncated portions of an antibody's heavy and light chain sequences (e.g., mAB 3E10) as needed to maintain the functional integrity of the attached MBNL polypeptide. Further still, the targeting moiety can be linked to an exposed internal (non-terminus) residue of MBNL or a variant thereof. In further embodiments, any combination of the MBNL-targeting moiety configurations can be employed, thereby resulting in an MBNL: targeting moiety ratio that is greater than 1:1 (e.g., two MBNL molecules to one targeting moiety).

The MBNL polypeptide and the targeting moiety may be linked directly to each other. Alternatively, they may be linked to each other via a linker sequence, which separates the MBNL polypeptide and the targeting moiety by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional domains of the MBNL polypeptide or the targeting moiety, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In a specific embodiment, a linker sequence length of about 20 amino acids can be used to provide a suitable separation of functional protein domains, although longer or shorter linker sequences may also be used. The length of the linker sequence separating the MBNL polypeptide and the targeting moiety can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. In other embodiments, the linker joining the MBNL polypeptide to an targeting moiety can be a constant domain of an antibody (e.g., constant domain of mAb 3E10 or all or a portion of an Fc region of another antibody). In certain embodiments, the linker is a cleavable linker.

In other embodiments, the MBNL polypeptide or functional fragment thereof may be conjugated or joined directly to the targeting moiety. For example, a recombinantly conjugated chimeric polypeptide can be produced as an in-frame fusion of the MBNL portion and the targeting moiety portion. In certain embodiments, the linker may be a cleavable linker. In any of the foregoing embodiments, the targeting moiety may be conjugated (directly or via a linker) to the N-terminal or C-terminal amino acid of the MBNL polypeptide. In other embodiments, the targeting moiety may be conjugated (directly or indirectly) to an internal amino acid of the MBNL polypeptide. Note that the two portions of the construct are conjugated/joined to each other. Unless otherwise specified, describing the chimeric polypeptide as a conjugation of the MBNL portion to the targeting moiety is used equivalently as a conjugation of the targeting moiety to the MBNL portion.

In certain embodiments, the chimeric polypeptides of the present invention can be generated using well-known cross-linking reagents and protocols. For example, there are a large number of chemical cross-linking agents that are known to those skilled in the art and useful for cross-linking the MBNL polypeptide with a targeting moiety (e.g., an antibody). For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-toluene (SMPT), N-succinimidyl 3-(2-pyridyldithio)propionate (SPDP), succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this invention. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain specific embodiments, chimeric polypeptides of the invention can be produced by using a universal carrier system. For example, an MBNL polypeptide can be conjugated to a common carrier such as protein A, poly-L-lysine, hex-histidine (SEQ ID NO: 17), and the like. The conjugated carrier will then form a complex with an antibody which acts as a targeting moiety. A small portion of the carrier molecule that is responsible for binding immunoglobulin could be used as the carrier.

In certain embodiments, chimeric polypeptides of the invention can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of cross-linking for chemical conjugation of MBNL to an targeting moiety, a cleavable domain or cleavable linker can be used. Cleavage will allow separation of the targeting moiety and the MBNL polypeptide. For example, following penetration of a cell by a chimeric polypeptide, cleavage of the cleavable linker would allow separation of MBNL from the targeting moiety.

In certain embodiments, the chimeric polypeptides of the present invention can be generated as a fusion protein containing a MBNL polypeptide and a targeting moiety (e.g., an antibody or a homing peptide), expressed as one contiguous polypeptide chain. In preparing such fusion protein, a fusion gene is constructed comprising nucleic acids which encode an MBNL polypeptide and a targeting moiety, and optionally, a peptide linker sequence to span the MBNL polypeptide and the targeting moiety. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339: 68, incorporated by reference herein. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The chimeric polypeptides encoded by the fusion gene may be recombinantly produced using various expression systems as is well known in the art (also see below).

Recombinantly conjugated chimeric polypeptides include embodiments in which the MBNL polypeptide is conjugated to the N-terminus or C-terminus of the targeting moiety.

In some embodiments, the immunogenicity of the chimeric polypeptide may be reduced by identifying a candidate T-cell epitope within a junction region spanning the chimeric polypeptide and changing an amino acid within the junction region as described in U.S. Patent Publication No. 2003/0166877.

Chimeric polypeptides according to the invention can be used for numerous purposes. We note that any of the chimeric polypeptides described herein can be used in any of the methods described herein, and such suitable combinations are specifically contemplated.

Chimeric polypeptides described herein can be used to deliver MBNL polypeptide to cells, particular to a muscle cell. Thus, the chimeric polypeptides can be used to facilitate transport of MBNL to cells in vitro or in vivo. By facilitating transport to cells, the chimeric polypeptides improve delivery efficiency, thus facilitating working with MBNL polypeptide in vitro or in vivo. Further, by increasing the efficiency of transport, the chimeric polypeptides may help decrease the amount of MBNL needed for in vitro or in vivo experimentation.

The chimeric polypeptides can be used to study the function of MBNL in cells in culture, as well as to study transport of MBNL. The chimeric polypeptides can be used to identify binding partners for MBNL in cells. The chimeric polypeptides can be used to help treat or aleviate the symptoms of myotonic dystrophy in humans or in an animal model. The foregoing are merely exemplary of the uses for the subject chimeric polypeptides.

IV. MBNL-Related Nucleic Acids And Expression

In certain embodiments, the present invention makes use of nucleic acids for producing an MBNL polypeptide (including functional fragments, variants, and fusions thereof). In certain specific embodiments, the nucleic acids may further comprise DNA which encodes a targeting moiety (e.g., an antibody or a homing peptide) for making a recombinant chimeric protein of the invention. All these nucleic acids are collectively referred to as MBNL nucleic acids.

The nucleic acids may be single-stranded or double-stranded, DNA or RNA molecules. In certain embodiments, the disclosure relates to isolated or recombinant nucleic acid sequences that are at least 80%, 85%, 90%, 95%, 97%, 98%, 99% or 100% identical to a region of an MBNL1 nucleotide sequence (e.g., GenBank Accession Nos.: NM_021038.3, NM_207292.1, NM_207293.1, NM_207294.1, NM_207295.1, NM_207296.1, and NM_207297.1), an MBNL2 nucleotide sequence (e.g., GenBank Accession Nos.: NM_144778.2 and NM_207304.1), and an MBNL3 nucleotide sequence (e.g., GenBank Accession Nos.: NM_018388.2 and NM_133486.1). In further embodiments, the MBNL nucleic acid sequences can be isolated, recombinant, and/or fused with a heterologous nucleotide sequence, or in a DNA library.

In certain embodiments, MBNL nucleic acids also include nucleotide sequences that hybridize under highly stringent conditions to any of the above-mentioned native MBNL nucleotide sequence (e.g., GenBank Accession Nos.: NM_021038.3, NM_207292.1, NM_207293.1, NM_207294.1, NM_207295.1, NM_207296.1, NM_207297.1, NM_144778.2, NM_207304.1, NM_018388.2, and NM_133486.1), or complement sequences thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the native MBNL nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant MBNL nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this invention relates to an expression vector comprising a nucleotide sequence encoding an MBNL polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

In some embodiments, a nucleic acid construct, comprising a nucleotide sequence that encodes an MBNL polypeptide or a bioactive fragment thereof, is operably linked to a nucleotide sequence that encodes a targeting moiety, wherein the nucleic acid construct encodes a chimeric polypeptide having MBNL biological activity. In certain embodiments, the nucleic acid constructs may further comprise a nucleotide sequence that encodes a linker.

This invention also pertains to a host cell transfected with a recombinant gene which encodes an MBNL polypeptide or a chimeric polypeptide of the invention. The host cell may be any prokaryotic or eukaryotic cell. For example, an MBNL polypeptide or a chimeric polypeptide may be expressed in bacterial cells such as *E. coli*, insect cells (e.g., using a baculovirus expression system), yeast, or mammalian cells. Other suitable host cells are known to those skilled in the art.

The present invention further pertains to methods of producing an MBNL polypeptide or a chimeric polypeptide of the invention. For example, a host cell transfected with an expression vector encoding an MBNL polypeptide or a chimeric polypeptide can be cultured under appropriate conditions to allow expression of the polypeptide to occur. The polypeptide may be secreted and isolated from a mixture of cells and medium containing the polypeptides. Alternatively, the polypeptides may be retained cytoplasmically or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., an MBNL polypeptide). In a preferred embodiment, the polypeptide is a fusion protein containing a domain which facilitates its purification.

A recombinant MBNL nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

V. Methods of Treatment

For any of the methods described herein, the disclosure contemplates the use of any of the chimeric polypeptides described throughout the application. In addition, for any of the methods described herein, the disclosure comtemplates the combination of any step or steps of one method with any step or steps from another method.

In certain embodiments, the present invention provides methods of treating conditions associated with aberrant microsatellite expansion, such as myotonic dystrophy. These methods involve administering to the individual a therapeutically effective amount of a chimeric polypeptide as described above. These methods are particularly aimed at therapeutic and prophylactic treatments of animals, and more particularly, humans. With respect to methods for treating myotonic dystrophy, the disclosure contemplates all combinations of any of the foregoing aspects and embodiments, as well as combinations with any of the embodiments set forth in the detailed description and examples.

The present disclosure provides a method of delivering a chimeric polypeptide or nucleic acid construct into a cell via an equilibrative nucleoside transporter (ENT2) pathway, comprising contacting a cell with a chimeric polypeptide or nucleic acid construct. In certain embodiments, the method comprises contacting a cell with a chimeric polypeptide, which chimeric polypeptide comprises an MBNL polypeptide or bioactive fragment thereof and an targeting moiety which mediates transport across a cellular membrane via an ENT2 pathway, thereby delivering the chimeric polypeptide into the cell. In certain embodiments, the cell is amuscle cell. The muscle cells targeted using the claimed method may include skeletal, cardiac or smooth muscle cells.

The present disclosure also provides a method of delivering a chimeric polypeptide or nucleic acid construct into a cell via a pathway that allows access to cells other than muscle cells. Other cell types that could be targeted using the claimed method include, for example, neurons, epithelial cells, liver cells, kidney cells or Leydig cells.

Conditions associated with aberrant microsatellite expansion (also referred to herein as microsatellite expansion diseases) include a number of neurological and neuromuscular diseases (O'Donnell, et al., 2002, Annu Rev. Neurosci. 25: 315). These diseases or conditions are caused by microsatellite repeat expansions in coding and non-coding regions. These microsatellite repeat expansions may include, for example, CAG or CUG repeats, or variations thereof (e.g. CCUG). For example, the characterized coding region expansion diseases include *Dentatorubral pallidoluysian* atrophy (DRPLA), Huntington chorea (HD), Oculopharyngeal muscular dystrophy (OPMD), Spinobulbar muscular atrophy (SBMA), specific forms of Creutzfeldt-Jakob Disease and Spinocerebellar ataxia types 1, 2, 3, 6, 7, and 17 (SCAT, SCA2, SCA3, SCA6, SCAT, SCA17). The characterized non-coding region expansion diseases include Fragile XA, Fragile XE, Friedrich's ataxia, Myotonic Dystrophy type 1 (DM1), Myotonic Dystrophy type 2 (DM2), and Spinocerebellar ataxia types 8, 10, and 12 (SCA8, SCA10, SCA12). Huntington's disease-like type 2 (HDL2) is likewise caused by a microsatellite expansion. Familial schizophrenia and bipolar disorder also may be caused by microsatellite expansion (Saleem, 2001, Mol. Psychiatry, 6(6): 694-700). Microsatellite expansion diseases have been most commonly associated with trinucleotide expansion mutations. Microsatellite expansion diseases have also been associated with tetranucleotide and even pentanucleotide expansion mutations. Disease severity and age of onset have both been related to the size of the expansion mutation, eventually leading to muscle weakness and premature cataract formation, and, in severe cases, to hypotonia, muscle heart block, and nervous system dysfunction (Korade-Mirnics, et al., 1998, Nuc. Acids Res. 26(6): 1363-1368). In certain embodiments, the claimed method may be used to treat any one of the diseases listed above.

Myotonic dystrophy (DM) is an autosomal dominant neuromuscular disease which is the most common form of muscular dystrophy affecting adults. The clinical picture in DM is well established but exceptionally variable. Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy. The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form, which occurs congenitally, is associated with generalized muscular hypoplasia, mental retardation, and high neonatal mortality.

Myotonic dystrophy type 1 (DM1) is caused by a trinucleotide $(CTG)_n$ expansion (n=50 to >3000) in the 3'-untranslated region (3'UTR) of the Dystrophia myotonica-protein kinase (DMPK) gene. Myotonic dystrophy type 2 (DM2) is caused by a tetranucleotide $(CCTG)_n$ expansion (n=75 to about 11,000) in the first intron of zinc finger protein 9 (ZNF9) gene (Ranum, et al., 2002, Curr. Opin. in Genet. and Dev. 12:266-271). There appears to be a common pathogenic mechanism involving the accumulation of transcripts into discrete nuclear RNA foci containing long tracts of CUG or CCUG repeats expressed from the expanded allele, and both DM1 and DM2 mutant transcripts accumulate as foci within muscle nuclei (Liguori, et al., 2001, Science 293: 864-867). Transgenic mice which express a large CTG repeat in the 3'-UTR of a human skeletal actin transgene develop myonuclear RNA foci, myotonia, and degenerative muscle changes similar to those seen in human DM (Mankodi, et al., 2000, Science 289: 1769-1773). The myotonia in such transgenic mice is caused by loss of skeletal muscle chloride (ClC-1) channels due to aberrant pre-mRNA splicing (Mankodi, et al., 2002, Mol. Cell. 10: 35-44). Similar ClC-1 splicing defects exist in DM1 and DM2.

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). For example, "treatment" of DM1 and DM2 encompasses a complete reversal or cure of the disease, or any range of improvement in conditions and/or adverse effects attributable to DM1 and DM2. Merely to illustrate, "treatment" of DM1 and DM2 includes an improvement in any of the following effects associated with DM1, DM2 or combination thereof: muscle weakness, muscle wasting, grip strength, cataracts, difficulty relaxing grasp, irregularities in heartbeat, constipation and other digestive problems, retinal degeneration, low IQ, cognitive defects, frontal balding, skin disorders, atrophy of the testicles, insulin resistance and sleep apnea. Improvements in any of these conditions can be readily assessed according to standard methods and techniques known in the art. Other symptoms not listed above may also be monitored in order to determine the effectiveness of treating DM1 or DM2. The population of subjects treated by the method of the disease includes subjects suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, one or more chimeric polypeptides of the present invention can be administered, together (simultaneously) or at different times (sequentially). In addition, chimeric polypeptides of the present invention can be administered alone or in combination with one or more additional compounds or therapies for treating myotonic dystrophy or for treating neuromuscular disorders in general. For example, one or more chimeric polypeptides can be co-administered in conjunction with one or more therapeutic compounds. When co-administration is indicated, the combination therapy may encompass simultaneous or alternating administration. In addition, the combination may encompass acute or chronic administration. Optionally, the chimeric polypeptide of the present invention and additional compounds act in an additive or synergistic manner for treating myotonic dystrophy. Additional compounds to be used in combination therapies include, but are not limited to, small molecules, polypeptides, antibodies, antisense oligonucleotides, and siRNA molecules. Depending on the nature of the combinatory therapy, administration of the chimeric polypeptides of the invention may be continued while the other therapy is being administered and/or thereafter. Administration of the chimeric polypeptides may be made in a single dose, or in multiple doses. In some instances, administration of the chimeric polypeptides is commenced at least several days prior to the other therapy, while in other instances, administration is begun either immediately before or at the time of the administration of the other therapy.

In another example of combination therapy, one or more chimeric polypeptides of the invention can be used as part of a therapeutic regimen combined with one or more additional treatment modalities. By way of example, such other treatment modalities include, but are not limited to, dietary therapy, occupational therapy, physical therapy, ventilator supportive therapy, massage, acupuncture, acupressure, mobility aids, assistance animals, and the like.

Note that although the chimeric polypeptides described herein can be used in combination with other therapies, in certain embodiments, a chimeric polypeptide is provided as the sole form of therapy. Regardless of whether administrated alone or in combination with other medications or therapeutic regiments, the dosage, frequency, route of administration, and timing of administration of the chimeric polypeptides is determined by a physician based on the condition and needs of the patient.

VI. Gene Therapy

Conventional viral and non-viral based gene transfer methods can be used to introduce nucleic acids encoding polypeptides of MBNL in mammalian cells or target tissues. Such methods can be used to administer nucleic acids encoding polypeptides of the invention (e.g., MBNL, including variants thereof) to cells in vitro. In some embodiments, the nucleic acids encoding MBNL are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of nucleic acids encoding MBNL or its variants take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SW), human immuno deficiency virus (HIV), and combinations thereof, all of which are well known in the art.

In applications where transient expression of the polypeptides of the invention is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures. Construction of recombinant AAV vectors are described in a number of publications, including U.S. Pat. No. 5,173,414; Tratschin et al., *Mol. Cell. Biol.* 5:3251-3260 (1985); Tratschin, et al.; *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity.

Packaging cells are used to form virus particles that are capable of infecting a host cell. Such cells include 293 cells, which package adenovirus, and 42 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells, such as muscle cells.

Gene therapy vectors can be delivered in vivo by administration to an individual patient, by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. For example, cells are isolated from the subject organism, transfected with a nucleic acid (gene or cDNA) encoding, e.g., MBNL or its variants, and re-infused back into the subject organism (e.g., patient). Various cell types suitable for ex vivo transfection are well known to those of skill in the art.

In certain embodiments, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Stem cells are isolated for transduction and differentiation using known methods.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described herein.

VII. Methods of Administration

Various delivery systems are known and can be used to administer the chimeric polypeptides of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction can be enteral or parenteral, including but not limited to, intradermal, intramuscular, intraperitoneal, intravenous, subcutaneous, pulmonary, intranasal, intraocular, epidural, and oral routes. The chimeric polypeptides may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including epidural injection, intranasal administration or intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In certain embodiments, it may be desirable to administer the chimeric polypeptides of the invention locally to the area in need of treatment (e.g., muscle); this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In certain embodiments, it may be desirable to administer the chimeric polypeptides locally, for example, to the eye using ocular administration methods. In another embodiments, such local administration can be to all or a portion of the heart. For example, administration can be by intrapericardial or intramyocardial administration. Similarly, administration to cardiac tissue can be achieved using a catheter, wire, and the like intended for delivery of agents to various regions of the heart.

In other embodiments, the chimeric polypeptides of the invention can be delivered in a vesicle, in particular, a liposome (see Langer, 1990, Science 249:1527-1533). In yet another embodiment, the chimeric polypeptides of the invention can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, the chimeric polypeptides of the invention can be delivered intravenously.

In certain embodiments, the chimeric polypeptides are administered by intravenous infusion. In certain embodiments, the chimeric polypeptides are infused over a period of at least 10, at least 15, at least 20, or at least 30 minutes. In other embodiments, the chimeric polypeptides are infused over a period of at least 60, 90, or 120 minutes. Regardless of the infusion period, the invention contemplates that each infusion is part of an overall treatment plan where chimeric polypeptide is administered according to a regular schedule (e.g., weekly, monthly, etc.).

VIII. Pharmaceutical Compositions

In certain embodiments, the subject chimeric polypeptides of the present invention are formulated with a pharmaceutically acceptable carrier. One or more chimeric polypeptides can be administered alone or as a component of a pharmaceutical formulation (composition). The chimeric polypeptides may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject chimeric polypeptides include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic agents and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more chimeric polypeptide therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In particular, methods of the invention can be administered topically, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a subject chimeric polypeptides, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more chimeric polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In a preferred embodiment, the chimeric polypeptides of the present invention are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the chimeric polypeptides of the invention which will be effective in the treatment of a tissue-related condition or disease (e.g., myotonic dystrophy) can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of the active chimeric polypeptide per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

IX. Animal Models

Mice possessing a targeted inactivation of the MBNL1 gene (MBNL1−/−) display myotonia starting around 6 weeks of age (Kanadia et al., 2003, Science, 302: 1978-1980). While MBNL−/−mice do not display the severe neonatal muscle weakness observed in congenital human cases of DM1, these mice do display delayed muscle relaxation, and electromyographic recordings taken from these mice indicate myotonic discharges (Kanadia, 2003). In addition, these mice have abnormal splicing of several genes, such as the Clcn1 and Tnnt2 genes (Kanadia, 2003). A corresponding decrease in CIC-1, the protein encoded by the Clcn1 gene, also is observed in these mice compared to a wildtype mouse (Kanadia, 2003). These mice also display pathological features in muscle tissue, including an increase in cellular nuclei in muscle cells and a splitting of myofibers (Kanadia, 2003). In addition, and similar to many human cases of DM1, distinctive ocular cataracts were observed in the MBNL KO animals (Kanadia, 2003).

Mice possessing a targeted inactivation of the MBNL2 gene (MBNL2−/−) display myotonia starting around 6 months of age (Hao, et al., 2008, Developmental Dynamics, 237: 403-410). Similar to the MBNL1−/−model, the MBNL2−/−model also displays the delayed muscle relaxation and myotonic electromyographic recordings (Hao, 2008). These MBNL2−/−mice also have abnormal spinal curvature or lordosis (Hao, 2008). These mice also have more central nuclei in skeletal muscle cells, a decrease in muscle cell size and an increase in collagen levels and fibrosis in skeletal muscle (Hao, 2008). A significant RNA processing defect of the Clcn1 gene was also observed in the MBNL2−/−mice, which correlated with a significant decrease in CIC-1 protein in certain areas of the skeletal muscle (Hao, 2008).

As discussed above, DM is caused by a CTG repeat expansion in the 3' untranslated region of the gene encoding MBNL, DMPK. A mouse model engineered to inducibly express in skeletal muscle the DMPK gene containing large tracts of CTG repeats displayed several features observed in human cases of DM1 disease (Orengo et al., 2008, PNAS, 105(7): 2646-2651). These DMPK-CTG mice possess DPMK-CUG RNA colocalizing with MBNL1 protein, display defective splicing events and possess an increase in the levels of CUGBP1, a splicing factor associated with regulating alternative splicing events in DM1 disease in humans (Orengo, 2008). In addition, these mice display myotonic electromyograms (Orengo, 2008). These mice also display severe and progressive skeletal muscle wasting and a dramatic loss of muscle function (Orengo, 2008).

A mouse model engineered to express the human skeletal actin (HSA) gene with an untranslated CTG repeat (HSAlr41 mouse) in skeletal muscle has also been generated as a model of myotonic dystrophy. This model is associated with ~40% mortality by 44 weeks of age (Mankodi, 2000, Science, 289: 1769-1772). In addition, these mice also display myotonic discharges and abnormal hind-limb posture during the initiation of movement (Mankodi, 2000). These mice also have an increase in central nuclei and ring fibers and variability in fiber size in skeletal muscle, as well as an up-regulated activity of proteins involved in oxidative muscle fibers, succinate dehydrogenase and cytochrome oxidase (Mankodi, 2000). The long-repeat transcripts of the HSA gene are also found to be retained within the nuclei of these HSAlr41 mice (Mankodi, 2000). These mice do not display significant muscle wasting or weakness (Mankodi, 2000).

Accordingly, in certain embodiments, the present disclosure contemplates methods of surveying improvements in disease phenotypes using the MBNL constructs (e.g., the chimeric polypeptides comprising MBNL) disclosed herein in any one or more animal models, such as the mouse models described herein. By way of example, various parameters can be examined in experimental animals treated with a subject chimeric polypeptide, and such animals can be compared to controls. Exemplary parameters that can be assessed to evaluate potential efficacy include, but are not limited to: increase in lifespan; increase in muscle size; weight gain; decrease in myotonic behavior (e.g., closer to normal levels of muscle relaxation); improvements in myocardiogram results (e.g., decrease in myotonic discharges); improved scores on treadmill tests; improved gait; decrease in the number of nuclei in skeletal muscle; decrease in aberrant splicing events; decreased levels of CUGBP1; normal or improved spinal curvature; decrease in activity of proteins involved in oxidative muscle fibers; decrease in number of myofiber splitting events; increase in ClC-1 protein levels and Clcn1 RNA levels.

Moreover, once it is established that, for example, 3E10*MBNL or 3E10-GS3-MBNL results in an improvement in any one or more of these phenotypes, a complete pharmacokinetic study to determine the effective dose, clearance rate, volume of distribution, and half-life of 3E10-MBNL can be determined. The pharmacokinetics of 3E10-MBNL will likely follow a multi-compartment model in which various tissues exhibit different degrees of clearance, and simple assessments of serum half-life will not provide sufficient information to calculate a therapeutic dosing rate. Therefore, the calculation of a dose and dosing rate will ultimately be derived from empirical observations of the pharmacokinetics, pharmacodynamics, toxicology of a given dose of 3E10-MBNL, and the rate and extent to which an increase in lifespan, treadmill time, ClC-1 levels, for example, or decrease in aberrant splicing events, myotonia, muscle wasting, for example, are observed. The dose and dosing rate of 3E10-MBNL determined in a subsequent pharmacokinetic study can be used as the standard comparator to evaluate optimized lots of, for example, recombinant 3E10-MBNL or other such chimeric protein products. The PK/PD/TK of the final product can then be examined in larger animals such as rats, dogs, and primates.

The above mouse models provide a suitable animal model system for assessing the activity and effectiveness of the subject chimeric polypeptides. These models have correlations with symptoms of DM1 or DM2, and thus provide appropriate models for studying myotonic dystrophy. Activity of the polypeptide can be assessed in these mouse models, and the results compared to that observed in wildtype control animals and animals not treated with the chimeric polypeptides. Similarly, the subject chimeric polypeptides can be evaluated using cells in culture, for example, cells prepared from the mutant mice.

X. Kits

In certain embodiments, the invention also provides a pharmaceutical package or kit comprising one or more containers filled with at least one chimeric polypeptide of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

EXEMPLIFICATION

The invention now being generally described, it will be more readily understood by reference to the following examples, which are included merely for purposes of illustration of certain aspects and embodiments of the present invention, and are not intended to limit the invention. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1

Chemical Conjugation of 3E10 and hMBNL1 (mAb3E10*hMBNL1)

Chemical Conjugation

Monoclonal Ab 3E10 is of the IgG2a subtype and is derived from the fusion of spleen cells from an MRL/lpr/mpj mouse with FOX-NY hybridoma cells (Mankodi A et al., Mol. Cell. 2002 July; 10(1): 35-44. Ten milligrams (10 mg) of mAb 3E10 (regardless of whether isolated from a hybridoma or produced recombinantly and regardless of whether a native 3E10 or a variant that retains the properties of 3E10) will be conjugated covalently to 41 kDa human MBNL1 (Genecopia) in a 1/1 molar ratio with the use of two different heterobifunctional reagents, succinimidyl 3-(2-pyridyldithio) propionate and succinimidyl trans-4-(maleimidylmethyl)cyclohexane-1-carboxylate. This reaction modifies the lysine residues of mAb3E10 into thiols and adds thiolreactive maleimide groups to MBNL 1 (Weisbart R H, et al., J. Immunol. 2000 Jun. 1; 164(11): 6020-6). After deprotection, each modified protein will be reacted to each other to create a stable thioether bond. Chemical conjugation will be performed, and the products will be fractionated by gel filtration chromatography. The composition of the fractions will be assessed by native and SDS-PAGE in reducing and nonreducing environments. Fractions containing the greatest ratio of 3E10-MBNL1 conjugate to free 3E10 and free MBNL1 will be pooled and selected for use in later studies.

Similarly, conjugates will be made in which an antigen binding portion of 3E10 (such as a single chain Fv fragment) is conjugated to an MBNL1 polypeptide. Other exemplary conjugates include conjugates in which the targeting moiety is either a full length 3E10 mAb, or variant thereof, or an antigen binding fragment of the foregoing and in which the MBNL portion is an MBNL1, MBNL2, or MBNL3 polypeptide, or functional fragment of any of the foregoing. The foregoing methods can be used to make chemical conjugates that include any combination of MBNL portions and targeting moiety portions, and the foregoing are merely exemplary. Moreover, the experimental approach detailed herein can be used to test any such chimeric polypeptide In Vitro Assessment of Chemically Conjugated 3E10 and MBNL1

Ten to 100 uM of chemically conjugated 3E10-MBNL1, an unconjugated mixture of mAb 3E10 and MBNL1, mAb 3E10 alone, or MBNL1 alone will be applied to semiconfluent, undifferentiated DM1 or wildtype myoblasts (Table 1). Previous studies have shown that these myoblasts show splicing defects that are characteristic of DM1, though generally not as extreme as those observed in muscle tissue (Dansithong et al. J Biol. Chem. 2005 Feb. 18; 280(7):5773-80). The specificity of 3E10-GS3-MBNL40 for the ENT2 transporter will be validated by addition of nitrobenzylmercaptopurine riboside (NBMPR), an ENT2 specific inhibitor (Hansen et al., 2007, J. Biol. Chem., 282(29): 20790-3) to ENT2 transfected cells just prior to addition of 3E10-MBNL1. Eight to 24 hours later the media and cells will be collected for immunoblot and RTPCR analysis. A duplicate experiment will apply each of the above proteins onto DM1 and wildtype myoblasts grown on coverslips, followed by fixation and immunohistochemical detection of mAb3E10 using antibodies against mouse kappa light chain (Jackson Immunoresearch) and MBNL1 (Kanadia et al., 2006, Proc. Natl. Acad. Sci. USA, 103(31): 11748-53).

i) Immunoblot Detection of Cell Penetrating 3E10 and MBNL

Cell pellets will be resuspended in 500 ul PBS, lysed, and the supernatants will be collected for immunoblot analysis of mAb3E10 and MBNL1 as previously described (Kanadia et al., 2006, Proc. Natl. Acad. Sci. USA, 103(31):11748-53). Epitope tagging will not be employed, therefore the presence of a coincident anti-3E10 and anti-MBNL1 immunoreactive band of ~190 kDa (for the full length 3E10+full length MBNL) in 3E10*MBNL1 treated cells versus 3E10-alone and MBNL1-alone controls will constitute successful penetration of chemically conjugated 3E10*MBNL1. Tubulin detection will be used as a loading control.

ii) Immunofluorescence of Cell Penetrating 3E10 and MBNL

Coverslips of treated cells will be washed, fixed in 100% ethanol, rehydrated, and 3E10 and MBNL1 will be detected with previously described antibodies (Kanadia et al., 2003, Science, 302: 1978-80), followed by a horseradish peroxidase conjugated secondary antibody, color development, and viewing by light microscopy.

iii) RTPCR: MBNL1 Mediated Correction of Spliceopathy in DM1 Cells

Total RNA from treated DM1 and wildtype myoblasts will be purified using Trizol reagent and quantified using a spectrophotometer. To assess if MBNL1 is removing fetal exons from DM1 myoblasts we will use RTPCR employing a series of previously validated primers that coamplify fetal and adult mRNAs (Kanadia et al., 2006, Proc Natl Acad Sci USA, 103(31): 11748-53; Derossi et al., 1994, J Biol Chem, 269 (14): 10444-50; Vicente et al., 2007, Differentiation, 75(5): 427-40; Yuan et al., 2007, Nucleic Acids Res, 35(16): 5474-86; Weisbart et al., 1990, J Immunol, 144(7): 2653-8; Mankodi et al., 2005, Circ Res, 97(11): 1152-5; Ashizawa et al., 1993, Neurology, 43(12): 2674-8). Following gel electrophoresis of the RTPCR products, the relative abundance of fetal and adult PCR products will be compared against wildtype and DM1 myoblasts treated with 3E10-alone and MBNL1-alone. An increase in the amount of adult versus fetal PCR products in 3E10*MBNL1 treated DM1 myoblasts will constitute successful MBNL1 activity and warrant the

TABLE 1

Strategy to Assess Chemically Conjugated mAb 3E10 to human MBNL1

| Group | Cells | ENT2 Transfection | Treatment using recombinant protein | ENT2 Inhibitor | Cell Penetration | mRNA Splicing |
|---|---|---|---|---|---|---|
| 1 | DM1 | − | mAb 3E10*MBNL40 (chemically conjugated) | − | ? | ? |
| 2 | DM1 | − | mAb 3E10 & MBNL40 (mixed unconjugated) | − | Yes | No |
| 3 | DM1 | − | mAb 3E10 alone | − | Yes | No |
| 4 | DM1 | − | MBNL1 alone | − | No | No |
| 5 | DM1 | + | mAb 3E10*MBNL40 (chemically conjugated) | − | ? | ? |
| 6 | DM1 | + | mAb 3E10 & MBNL40 (mixed unconjugated) | − | Yes | No |
| 7 | DM1 | + | mAb 3E10 alone | − | Yes | No |
| 8 | DM1 | + | MBNL1 alone | − | No | No |
| 9 | DM1 | + | mAb 3E10*MBNL40 (chemically conjugated) | + | No | No |
| 10 | DM1 | + | mAb 3E10 & MBNL40 (mixed unconjugated) | + | No | No |
| 11 | DM1 | + | mAb 3E10 alone | + | No | No |
| 12 | DM1 | + | MBNL1 alone | + | No | No |
| 13 | WT | − | mAb 3E10*MBNL40 (chemically conjugated) | − | ? | Yes |
| 14 | WT | − | mAb 3E10 & MBNL40 (mixed unconjugated) | − | Yes | Yes |
| 15 | WT | − | mAb 3E10 alone | − | Yes | Yes |
| 16 | WT | − | MBNL1 alone | − | No | Yes | genetic conjugation of 3E10 to MBNL1 as well as the subsequent in vivo assessments of chemically conjugated 3E10*MBNL1. Samples of PCR products will be cut with sequence specific restriction enzymes to verify the identity of each PCR product and we will also include water only amplifications as negative controls. The band size of an adult or fetal PCR product of a given gene will be normalized to take into account the effect of greater fluorescence in larger ethidium bromide stained PCR products.

Other assays include assays to confirm that the conjugate can bind to CUG repeats

Example 2

Genetic Construct of fv 3E10 and hMBNL1 (Fv3E10-GS3-MBNL40)

Mammalian expression vectors encoding a genetic fusion of Fv3E10 and hMBNL40 (fv3E10-GS3-hMBNL40, comprising the scFv of mAb 3E10 fused to hMBNL40 by the GS3 linker) will be generated. Note that in the examples, we have used "Fv3E10" to refer to an scFv of 3E10. Following transfection, the conditioned media will also be immunoblotted to detect secretion of 3E10 and hMBNL1 into the culture media. Following concentration of the conditioned media the relative abundance of fetal and adult PCR products from DM1 myoblasts will be measured and compared to the appropriate controls (see Example 1) to further validate that the secreted Fv3E10-GS3-hMBNL40 enters cells and retains the ability to remove fetal exons. Note that these genetic fusions are also referred to as recombinant conjugates or recombinantly produced conjugates.

Additional recombinantly produced conjugates will similarly be made for later testing. By way of non-limiting example: (a) hMBNL40-GS3-3E10, (b) 3E10-GS3-hMBNL40, (c) hMBNL40-GS3-Fv3E10, (d) hMBNL40-3E10, (e) 3E10-hMBNL40, (f) hMBNL40-Fv3E10. Note that throughout the example, the abbreviation Fv is used to refer to a single chain Fv of 3E10. Similarly, mAb 3E10 and 3E10 are used interchangeably. These and other chimeric polypeptides can be tested using, for example, the assays detailed herein.

Create the cDNA for Human MBNL1 and Confirm Activity In Vitro i) Synthesis of the cDNA for 40 kDa MBNL1

The human MBNL1 cDNA encoding the 40 kDa peptide sequence is shown in SEQ ID NO: 2. The MBNL1 cDNA along with flanking restriction sites that facilitate cloning into appropriate expression vectors will be synthesized and sequenced by Genscript or other qualified manufacturer of gene sequences. To maximize expression, the MBNL1 cDNA will be codon optimized for mammalian and *pichia* expression. In the event that mammals or *pichia* prefer a different codon for a given amino acid, we will use the next best candidate to unify the preference. The resulting cDNA will be cloned into a CMV-based mammalian expression cassette and large scale preps of the plasmid pCMVhMBNL40 will be made using the Qiagen Mega Endo-free plasmid purification kit. To avoid complicating immune responses to the 3E10-MBNL1 protein we will not include any epitope or purification tags to the sequence.

ii) Transfection of Normal and DM1 Myoblasts In Vitro

The strategy to test the splicing of the MBNL1 is shown in Table 2. Ten micrograms of the plasmid pCMV (mock) or pCMV-hMBNL40 (MBNL1) will be transfected into normal and DM1 myoblasts using commercially available transfection reagents. To track the efficiency of transfection, duplicate transfections with plasmids encoding a suitable reporter such as beta-galactosidase or GFP will be performed. Forty-eight hours later transfected cells will be pelleted by centrifugation resuspended in 500 ul PBS and divided in two for protein and mRNA isolation.

TABLE 2

Strategy to Test Splicing by MBNL1

| Group | Cells | Transfected Plasmid | mRNA Splicing |
|---|---|---|---|
| 1 | DM1 | pCMV (Mock) | No |
| 2 | DM1 | pCMV-hMBNL40 (MBNL1) | ? |
| 3 | Normal | pCMV (Mock) | Yes |
| 4 | Normal | pCMV-hMBNL40 (MBNL1) | Yes | iii) Immunoblot Detection of Transfected Human MBNL 1, and Assay of MBNL 1 Mediated Correction of Spliceopathy in DM1 Cells The same procedures described in Example 1 will be utilized.

Create and Validate cDNA Fv3E10 Genetically Conjugated to 40 kDa Human MBNL1 i) Synthesis of the cDNA for Fv3E10

The cDNA encoding the mouse Fv3E10 variable light chain linked to the 3E10 heavy chain (SEQ ID NOs: 12-14) contains a mutation that enhances the cell penetrating capacity of the Fv fragment (Zack et al., 1996, J Immunol, 157(5): 2082-8). The 3E10 cDNA will be flanked by restriction sites that facilitate cloning in frame with the MBNL 1 cDNA, and synthesized and sequenced by Genscript or other qualified manufacturer of gene sequences. To maximize expression the 3E10 cDNA will be codon optimized for mammalian and *pichia* expression. In the event that mammals or *pichia* prefer a different codon for a given amino acid, the next best candidate to unify the preference will be used. The resulting cDNA will be cloned into a mammalian expression cassette and large scale preps of the plasmid pCMV-3E10-GS3-MBNL40 will be made using the Qiagen Mega Endo-free plasmid purification kit.

ii) Transfection of Normal and DM1 Cells In Vitro

The strategy to test the expression and mRNA splicing of the 3E10-GS3-MBNL40 genetic fusion is shown in Table 3. The transfection procedure will be the same as described above for transfection of the human MBNL1 cDNA. The conditioned media from the transfection in Table 3 will be used to test the secretion, uptake and splicing by 3E10-GS3-MBNL40 as shown in Table 4.

TABLE 3

Strategy to Test Expression and Splicing of 3E10-GS3-MBNL40

| Group | Cells | Transfected Plasmid | mRNA Splicing |
|---|---|---|---|
| 1 | DM1 | pCMV | No |
| 2 | DM1 | pCMV MBNL40 | Yes |
| 3 | DM1 | pCMV 3E10-GS3-MBNL40 | ? |
| 4 | WT | pCMV | Yes |
| 5 | WT | pCMV MBNL40 | Yes |
| 6 | WT | pCMV 3E10-GS3-MBNL40 | Yes |

TABLE 4

Strategy to Test Secretion, Uptake and Splicing of 3E10-MBNL1

| Group | Cells | ENT2 Transfection | Conditioned Media from Transfected Cells | ENT2 Inhibitor | mRNA Splicing |
|---|---|---|---|---|---|
| 1 | DM1 | − | pCMV (from group 4 Table 3) | − | No |
| 2 | DM1 | − | pCMV MBNL1 (from group 5 Table 3) | − | No |
| 3 | DM1 | − | pCMV 3E10-GS3-MBNL1 (from group 6 Table 3) | − | ? |
| 4 | DM1 | − | mAb 3E10*MBNL1 (chemical conjugate) | − | Yes |
| 5 | DM1 | + | pCMV (from group 4 Table 3) | + | No |
| 6 | DM1 | + | pCMV MBNL1 (from group 5 Table 3) | + | No |
| 7 | DM1 | + | pCMV 3E10-GS3-MBNL1 (from group 6 Table 3) | + | No |
| 8 | DM1 | + | mAb 3E10*MBNL1 (chemical conjugate) | + | No |
| 9 | DM1 | + | pCMV (from group 4 Table 3) | − | No |
| 10 | DM1 | + | pCMV MBNL1 (from group 5 Table 3) | − | No |
| 11 | DM1 | + | pCMV 3E10-GS3-MBNL1 (from group 6 Table 3) | − | ? |
| 12 | DM1 | + | mAb 3E10*MBNL1 (chemical conjugate) | − | Yes |
| 13 | WT | − | pCMV (from group 4 Table 3) | − | Yes |
| 14 | WT | − | pCMV MBNL1 (from group 5 Table 3) | − | Yes |
| 15 | WT | − | pCMV 3E10-GS3-MBNL1 (from group 6 Table 3) | − | Yes |
| 16 | WT | − | mAb 3E10*MBNL1 (chemical conjugate) | − | Yes | iii) Assessment of Secretion, Cell Uptake, and Splicing of 3E10-MBNL1

The 3E10 cDNA will possess the signal peptide of the variable kappa chain and should drive secretion of the 3E10-MBNL1 genetic conjugate. The secretion of 3E10-MBNL1 by transfected cells will be detected by immunoblot of conditioned media. To assess uptake of 3E10-GS3-MBNL40 and correction of splicing, conditioned media from the transfections shown in Table 3 will be applied to untransfected cells as shown in Table 4. Conditioned media from pCMV (mock) transfected and pCMV-MBNL40 transfected cells will serve as negative controls. Protein extracts from pCMV 3E10-GS3-MBNL40 transfected cells will serve as a positive control for expression of 3E10-GS3-MBNL40. Twenty-four hours later total RNA from conditioned cells will be collected and RTPCR will be performed as in Example 1. If 3E10-GS3-MBNL40 is secreted into the media from transfected cells, and yet does improve the spliceopathy following application to untransfected DM1 myoblasts, DM1 myoblasts will be transfected with the ENT2 transporter cDNA (Hansen et al., 2007, J Biol Chem 282(29): 20790-3), followed two days later by addition of conditioned media. The specificity of 3E10-GS3-MBNL40 for the ENT2 transporter will be validated by addition of nitrobenzylmercaptopurine riboside (NBMPR), an ENT2 specific inhibitor (Pennycooke et al., 2001, Biochem Biophys Res Commun. 280(3): 951-9) to ENT2 transfected cells just prior to addition of 3E10-MBNL1.

iv) Immunoblot Detection of Transfected 3E10-MBNL1 and Evaluation of MBNL1 Mediated Correction of Spliceopathy in DM1 Cells The same procedures described in Example 1 will be used. Production of Recombinant 3E10 Genetically Conjugated to MBNL1 i) Construction of protein expression vectors for *pichia*. Plasmid construction, transfection, colony selection and culture of *Pichia* will use kits and manuals per the manufacturer's instructions (Invitrogen). The cDNAs for genetically conjugated 3E10-GS3-MBNL40 created and validated in specific aims 2A and 2B will be cloned into two alternative plasmids; PICZ for intracellular expression and PICZalpha for secreted expression. Protein expression form each plasmid is driven by the AOX1 promoter. Transfected *pichia* will be selected with Zeocin and colonies will be tested for expression of recombinant 3E10-GS3-MBNL40. High expressers will be selected and scaled for purification.

ii) Purification of Recombinant 3E10-GS3-MBNL1 cDNA fusions with mAb 3E10 Fv are ligated into the yeast expression vector pPICZA which is subsequently electroporated into the *Pichia pastoris* X-33 strain. Colonies are selected with Zeocin (Invitrogen, Carlsbad, Calif.) and identified with anti-his6 antibodies (Qiagen Inc, Valencia, Calif.). X-33 cells are grown in baffled shaker flasks with buffered glycerol/methanol medium, and protein synthesis is induced with 0.5% methanol according to the manufacturer's protocol (EasySelect *Pichia* Expression Kit, Invitrogen, Carlsbad, Calif.). The cells are lysed by two passages through a French Cell Press at 20,000 lbs/in2, and recombinant protein is purified from cell pellets solubilized in 9M guanidine HCl and 2% NP40 by immobilized metal ion affinity chromatography (IMAC) on Ni-NTAAgarose (Qiagen, Valencia, Calif.). Bound protein is eluted in 50 mM NaH2PO4 containing 300 mM NaCl, 500 mM imidazole, and 25% glycerol. Samples of eluted fractions are electrophoresed in 4-20% gradient SDSPAGE (NuSep Ltd, Frenchs Forest, Australia), and recombinant proteins is identified by Western blotting to nitrocellulose membranes developed with cargo-specific mouse antibodies followed by alkalinephosphatase-conjugated goat antibodies to mouse IgG. Alkaline phosphatase activity is measured by the chromogenic substrate, nitroblue tetrazolium chloride/5-bromo-4-chloro-3-indolylphosphate p-toluidine salt. Proteins are identified in SDS-PAGE gels with GelCode Blue Stain Reagent (Pierce Chemical Co., Rockford, Ill.). Eluted protein is concentrated, reconstituted with fetal calf serum to 5%, and exchange dialyzed 100-fold in 30,000 MWCO spin filters (Millipore Corp., Billerica, Mass.) against McCoy's medium (Mediatech, Inc., Herndon, Va.) containing 5% glycerol.

iii) Quality assessment and formulation

Immunoblot against 3E10 and MBNL1 will be used to verify the size and identity of recombinant proteins, followed by silver staining to identify the relative purity of among preparations of 3E10, MBNL1 and 3E10-GS3-MBNL1. Recombinant material will be formulated in a buffer and concentration (~0.5 mg/ml) that is consistent with the needs of subsequent in vivo administrations.

iv) In Vitro Assessment of Recombinant Material

The amount of 3E10-GS3-MBNL1 in the conditioned media that alleviates the spliceopathy in DM1 cells will be determined using the methods described above. This value will be used as a standard to extrapolate the amount of *pichia*-derived recombinant 3E10-GS3-MBNL1 needed to alleviate the spliceopathy. As shown in Table 5 we will compare the relative splicing activity of mammalian cell-derived and *pichia*-derived recombinant 3E10-GS3-MBNL1 on DM1 and wildtype myoblasts.

homozygous mice (+/+) will be administered. Homozygous MBNL1 KO (−/−) and wildtype (+/+) mice are C57BL6 congenic.

TABLE 5

Strategy to Test Secretion, Uptake and Splicing from recombinant 3E10-MBNL1

| Group | Cells | ENT2 Transfection | Treatment using recombinant protein | ENT2 Intibitor | mRNA Splicing |
|---|---|---|---|---|---|
| 1 | DM1 | − | mAb 3E10*MBNL1 (chemical conjugate) | − | Yes |
| 2 | DM1 | − | 3E10-GS3-MBNL40 (genetically conjugated, from pichia) | − | ? |
| 3 | DM1 | − | 3E10-GS3-MBNL40 (genetically conjugated, conditioned meda) | − | Yes |
| 4 | DM1 | + | mAb 3E10*MBNL1 (chemical conjugate) | − | Yes |
| 5 | DM1 | + | 3E10-GS3-MBNL40 (genetically conjugated, from pichia) | − | ? |
| 6 | DM1 | + | 3E10-GS3-MBNL40 (genetically conjugated, conditioned meda) | − | Yes |
| 7 | DM1 | + | mAb 3E10*MBNL1 (chemical conjugate) | + | No |
| 8 | DM1 | + | 3E10-GS3-MBNL40 (genetically conjugated, from pichia) | + | No |
| 9 | DM1 | + | 3E10-GS3-MBNL40 (genetically conjugated, conditioned meda) | + | No |
| 10 | WT | − | mAb 3E10*MBNL1 (chemical conjugate) | − | Yes |
| 11 | WT | − | 3E10-GS3-MBNL40 (genetically conjugated, from pichia) | − | Yes |
| 12 | WT | − | 3E10-GS3-MBNL40 (genetically conjugated, conditioned meda) | − | Yes |

Example 3

In Vivo Assessment of Muscle Targeted MBNL1 in MBNL1 KO Mice

Selection of a DM1 Mouse Model for Evaluation

The MBNL 1 KO mouse recapitulates DM1 in many ways and exhibits an early onset of disease (6 weeks of age). MBNL1 KO mice possess no CTG expansions and thus the sequestering effect of the polyCUG mRNAs could result in an underestimation of the amount of MBNL1 that would be needed to correct the spliceopathy in DM1 (Kanadia et al., 2003, Science, 302: 1978-1980). The MBNL1 KO mouse will not be immunologically tolerant to a recombinant MBNL1 therapy, though the tolerizing effect of preexisting MBNL2 or MBNL3 may mitigate an immune response. The advantage of using MBNL1 KO mice is our ability to use ELISA to track the tissue distribution 3E10-GS3-MBNL1 and MBNL KO mice exhibit a greater degree of fetal exon inclusion than HSAlr mice (Derossi et al., 1994, J Biol Chem, 269(14): 10444-50). The systemic spliceopathy in MBNL1KO mice also allows tracking if other tissues, besides skeletal muscle, are amenable to chemically conjugated (3E10*MBNL1) or genetically conjugated (3E10-GS3-MBNL1) therapy. Therefore, to maximize chances of a positive evaluation, 3E10 chemically and genetically conjugated to MBNL1 in the MBNL1 KO mouse model will be tested initially. To control whether a superphysiological level of MBNL1 is detrimental, 3E10-MBNL1 to wildtype MBNL1

Selection of Dose of MBNL1

There currently is no information regarding the stability, clearance rate, volume of distribution or half-life of the injected material in a DM1 mouse model, and doses applied to DM1 cell lines in vitro do not faithfully extrapolate to animals. Therefore, the evaluation dose of 3E10 chemically or genetically conjugated to MBNL1 delivered to DM1 mouse models must be determined empirically. To minimize the confounding effect of a neutralizing immune response to 3E10-GS3-MBNL1 and to maximize the ability to demonstrate a therapeutic effect, two high doses of 5 mg/kg of 3E10-GS3-MBNL1 delivered in one week (Table 6), followed by assessment of changes in disease endpoints, will be assessed. The evidence in the literature suggests that the spliceopathy in MBNL1 KO mice will respond quite rapidly to small changes in exogenous MBNL1 (Hum Mol. Genet. 2009 Apr. 15; 18(8):1471-81. Epub 2009 Feb. 17). The development of anti-3E10-MBNL antibodies will also be monitored. If it is established that intravenous 3E10*MBNL1 or 3E10-GS3-MBNL1 results in an improvement in spliceopathy, subsequent in vivo assessments in other mouse models will be initiated, followed by assessment of changes in electromyography, splicing of fetal exons, immunofluorescence detection of sarcolemmal ClC-1, and histology of skeletal muscle. A positive evaluation of 3E10*MBNL1 or 3E10-GS3-MBNL1 will justify the production of quantities of GLP-grade material needed to perform a more thorough pharmacology and toxicology assessment, and thus determine a dose and dosing range for pre-IND studies.

TABLE 6

In vivo dosing plan for chemically and genetically conjugated 3E10-MBNL1

| Group | Strain | Age (weeks) | # of mice | Treatment | Dose (mg/kg) |
|---|---|---|---|---|---|
| 1 | MBNL1 −/− | 10 | 5 | mAb 3E10*MBNL40 (chemically conjugate) | 5 |
| 2 | MBNL1 −/− | 10 | 5 | mAb 3E10 & MBNL40 (mixed unconjugated) | 5 |
| 3 | MBNL1 −/− | 10 | 5 | Fv 3E10-GS3-MBNL40 (genetically conjugated) | 5 |
| 4 | MBNL1 −/− | 10 | 5 | Vehicle | NA |
| 5 | MBNL1 +/+ | 10 | 5 | mAb 3E10*MBNL40 (chemically conjugate) | 5 |
| 6 | MBNL1 +/+ | 10 | 5 | mAb 3E10 & MBNL40 (mixed unconjugated) | 5 |
| 7 | MBNL1 +/+ | 10 | 5 | Fv 3E10-GS3-MBNL40 (genetically conjugated) | 5 |
| 8 | MBNL1 +/+ | 10 | 5 | Vehicle | NA |

Timepoint Information: Dose twice per week for 1 week. Daily observations. Bleed and sacrifice at 11 weeks of age. Collect all tissues for IHC, H&E, RNA and protein isolation Materials and Methods i) Injection of Chemically and Genetically Conjugated 3E10-MBNL1

3E10*MBNL1 or 3E10-GS3-MBNL1 will be formulated and diluted in a buffer that is consistent with intravenous injection (e.g. sterile saline solution or a buffered solution of 50 mM Tris-HCl, pH 7.4, 0.15 M NaCl). The amount of 3E10*MBNL1 or 3E10-GS3-MBNL1 given to each mouse will be calculated as follows: dose (mg/kg)×mouse weight (kg)×stock concentration (mg/ml)=volume (ml) of stock per mouse, q.s. to 100 ul with vehicle.

ii) Blood Collection

Blood will be collected by cardiac puncture at the time that animals are sacrificed for tissue dissection. Serum will be removed and frozen at −80° C. To minimize the effects of thawing and handling all analysis of 3E10*MBNL1 or 3E10-GS3-MBNL1 circulating in the blood will be performed on the same day.

iii) Tissue Collection and Preparation

Sampled tissues will be divided for immunoblot, RTPCR, formalin-fixed paraffin-embedded tissue blocks and frozen sections in OCT. One half of the heart, liver, lung, spleen, kidneys, quadriceps, EDL, soleus, diaphragm, and biceps will be subdivided and frozen in plastic tubes for further processing for immunoblot and RTPCR analysis. The remaining half of the heart, liver, lung, spleen, kidneys, quadriceps, EDL, soleus, diaphragm, and biceps will be subdivided, frozen in OCT tissue sectioning medium, or fixed in zinc-formaldehyde fixation for 24 to 48 hours at 4° C. and paraffin embedded.

iv) Histological Evaluation

Brightfield microscopy of HE sections will be used to determine the percentage of centrally nucleated myofibers from five randomly selected fields. At least 200 fibers will be counted per mouse per muscle group. Scoring of central nuclei, inflammation and necrosis of hematoxylin and eosin stained skeletal and cardiac sections will be performed. Controls will include vehicle and treated heterozygous MBNL1+/+mice and vehicle treated MBNL1−/−mice.

v) RNA Collection RTPCR: MBNL1 Mediated Correction of Spliceopathy in DM1 Cells

To be performed as described in Example 1, except tissues will be crushed in liquid nitrogen prior to extraction with Trizol reagent. Controls will include vehicle and treated heterozygous MBNL1+/+mice and vehicle treated MBNL1−/− mice.

vi) Immunofluorescence

Exogenously delivered MBNL1 will be detected using a rabbit polyclonal anti-MBNL1 antibody raised against a peptide that is 100% conserved in humans and mice, and detects no signal by immunofluorescence in MNBL1 knockouts (Hunley et al., 2004, Pediatrics, 114(4): e532-5). Ten micrometer frozen sections will be cut and placed on Superfrost Plus microscope slides. Detection of ClC-1, a chloride channel will be detected with a 1:1000 dilution of polyclonal anti-ClC-1 antibody that recognizes the C-terminus of ClC-1 (Alpha Diagnostic, San Antonio) followed by 1:1000 dilution of FITC-conjugated anti-rabbit secondary antibody (Jackson Immunoresearch). Controls will include vehicle and treated heterozygous MBNL1+/+mice and vehicle treated MBNL1−/−mice.

vii) Immunoblot

Immunoblot will be used to detect 3E10 and MBNL1 immune reactive material in 3E10-MBNL1 treated muscles and tissues. Protein isolation and immunoblot detection of 3E10 and MBNL1 will be performed as previously described (Kanadia et al., 2003, Science, 302: 1978-1980). MBNL1 will be detected with rabbit polyclonal A2764 antibody (Lin et al., 2006, Hum Mol Genet, 15(13): 2087-97). Antibody detection of blotted proteins will use NBT/BCIP as a substrate. Controls will include vehicle and treated heterozygous MBNL1+/+mice and vehicle treated MBNL1−/−mice.

viii) Analysis of circulating 3E10-MBNL1

An ELISA specific to human 3E10-MBNL1 will be developed and validated using available anti-human MBNL1 antibodies (Kanadia et al., 2006, Proc Natl Acad Sci USA 103 (31): 11748-53) and horseradish peroxidase conjugated anti-mouse secondary antibody (Jackson Immunoresearch). Recombinant 3E10-MBNL1 will be diluted and used to generate a standard curve. Levels of 3E10-MBNL1 will be determined from dilutions of serum (normalized to ng/ml of serum) or tissue extracts (normalized to ng/mg of tissue). Controls will include vehicle and treated heterozygous MBNL1+/+mice and vehicle treated MBNL1−/−mice. Monitoring of anti-3E10-MBNL1 antibody responses. Purified 3E10-MBNL1 used to inject MBNL1 KO mice will be plated onto high-binding 96 well ELISA plates at 1 ug/ml in coating buffer (Pierce Biotech), allowed to coat overnight, blocked for 30 minutes in 1% nonfat drymilk (Biorad) in TBS, and rinsed three times in TBS. Two-fold dilutions of sera from vehicle and 3E10-MBNL1 injected animals will be loaded into wells, allowed to incubate for 30 minutes at 37° C., washed three times, incubated with horseradish peroxidase (HRP)-conjugated rabbit anti-mouse IgA, IgG, and IgM, allowed to incubate for 30 minutes at 37° C., and washed three times. Mouse anti-3E10-MBNL1 antibodies will be detected with TMB liquid substrate and read at 405 nm in ELISA plate reader. Polyclonal rabbit antimouse MBNL1 (Kanadia et al., 2003, Science, 302: 1978-80), followed by HRP-conjugated goat anti-rabbit will serve as the positive control antibody reaction. Any absorbance at 405 nm greater than that of vehicle treated MBNL1 KO mice will constitute a positive anti-3E10-MBNL1 antibody response. Controls will include vehicle and treated heterozygous MBNL1+/+ mice and vehicle treated MBNL1−/−mice.

ix) Statistical Analysis

Pairwise comparisons will employ Student's t-test. Comparisons among multiple groups will employ ANOVA. In both cases a p-value <0.05 will be considered statistically significant.

Example 4

In Vivo Assessment of Muscle Targeted MBNL1 in HSAlr41 Mice

Example 4 will be performed exactly the same as Example 3, except that transgenic HSAlr41 mice with 3E10*MBNL1 or 3E10-GS3-MBNL1 will be injected, over a longer dosing period, followed by electromyographic and end of life histologic and spliceopathic assessments of skeletal muscle. In addition to immunofluorescence detection of MBNL1, fluorescent in situ hybridization (FISH) to determine if 3E10-MBNL1 has altered the distribution of nuclear RNA foci will also be performed. To control whether a superphysiological level of MBNL1 is detrimental, 3E10-MBNL1 will be administered to nontransgenic FVB mice. Homozygous transgenic HSAlr41 (+/+) and nontransgenic control mice are inbred on the FVB background.

i) Electrophysiology

Three days following the last of four doses of 3E10-GS3-MBNL1 electromyographic assessments of 3E10-MBNL1 treated HSALr41+/+ and FVB mice will be made as previously published (Mankodi et al., 2000, Science, 2000, 289

(5485): 1769-73) and under the supervision of the local IACUC protocol. Controls will include vehicle and treated FVB mice and vehicle treated HSAlr41+/+mice.

ii) Muscle Relaxation Test

Three days following the last of four doses of 3E10-GS3-MBNL1 muscle relaxation tests of 3E10-MBNL1 treated HSALr41+/+ and FVB mice will be made as previously published (Mankodi et al., 2000, Science, 2000, 289(5485): 1769-73) and under the supervision of the local IACUC protocol. Controls will include vehicle and treated FVB mice and vehicle treated HSAlr41+/+mice.

Example 5

In Vivo Assessment of Muscle Targeted MBNL2 in MBNL2−/− Mice

Example 5 will be performed as Examples 2 and 3, except that 3E10*MBNL2 or 3E10-GS3-MBNL2 will be generated and utilized, and treatment of MBNL2−/−mice will be assessed. The human MBNL2 cDNA encoding the MBNL2 peptide sequence is shown in SEQ ID NO: 2. MBNL2−/−mice also will be evaluated by electromyographic and end of life histologic and spliceopathic assessments of skeletal muscle similar to Example 4. MBNL2−/− mice also will be evaluated by examining spinal curvature.

Spinal Curvature

Spinal curvature will be quantified using X-ray radiograph analysis as described in Hao et al. (Hao, et al., 2008, Developmental Dynamics, 237: 403-410). Controls will include vehicle and treated FVB mice and vehicle treated MBNL2+/+ mice.

Example 6

In Vivo Assessment of Muscle Targeted MBNL1 in MBNL2−/− Mice

Example 6 will be performed exactly the same as Example 5, except that 3E10*MBNL1 or 3E10-GS3-MBNL1 will be generated and utilized for treatment of MBNL2−/−mice.

Example 7

In Vivo Assessment of Muscle Targeted MBNL1 in Inducible DMPK-CTG Mice

DMPK-CTG mice inducibly express the DMPK gene containing CTG repeats in the 5th exon. Tamoxifen treatment induces DMPK-CTG expression (Orengo et al., 2008, PNAS, 105(7): 2646-2651). DMPK-CTG mice will be 3-4 months of age before receiving 1 mg of tamoxifen injections daily for five days (Orengo, 2008). Following tamoxifen treatment, 3E10-GS3-MBNL1 treatment and subsequent treatment analysis will begin as described in Example 3. In addition, transgenic DMPK-CTG mice will be evaluated by electromyographic and end of life histologic and spliceopathic assessments of skeletal muscle similar to Example 4. Bitransgenic mice expressing no CTG repeats, or DMPK-CTG mice that did not receive tamoxifen treatment will be used as controls. Control or test mice will also receive either 3E10-GS3-MBNL1 treatment or vehicle control.

i) Immunoblot

In addition to the protein levels examined in Example 3 by immunoblot, CUGBP1 protein levels will also be examined, as described in Orengo et al.

ii)

DMPK-CTG mice will also be evaluated by a treadmill test as described in Orengo et al. Briefly, mice will be placed on a treadmill with rear electrical shock (e.g. AccuPacer Treadmill, AccuScan Instruments Inc.). The speed will be increased by 2 m/min every two minutes for 30 minutes or until mouse is unable to run.

The foregoing experimental scheme will similarly be used to evaluate other chimeric polypeptides. By way of non-limiting example, this scheme will be used to evaluate chemical conjugates and fusion proteins having an MBNL portion (or a fragment thereof, such as a fragment of approximately 260 amino acids—such as residues 1-260 of an MBNL protein) and a targeting moiety portion.

Exemplary Sequences

```
SEQ ID NO: 1 = The amino acid sequence of the
human MBNL1 protein, isoform a (GenBank
Accession No. NP_066368.2).
MAVSVTPIRDTKWLTLEVCREFQRGTCSRPDTECKFAHPSKSCQVENGRVIACFDSLK

GRCSRENCKYLHPPPHLKTQLEINGRNNLIQQKNMAMLAQQMQLANAMMPGAPLQP

VPMFSVAPSLATNASAAAFNPYLGPVSPSLVPAEILPTAPMLVTGNPGVPVPAAAAAA

AQKLMRTDRLEVCREYQRGNCNRGENDCRFAHPADSTMIDTNDNTVTVCMDYIKGR

CSREKCKYFHPPAHLQAKIKAAQYQVNQAAAAQAAATAAAMGIPQAVLPPLPKRPAL

EKTNGATAVFNTGIFQYQQALANMQLQQHTAFLPPGSILCMTPATSVVPMVHGATPA

TVSAATTSATSVPFAATATANQIPIISAEHLTSHKYVTQM

SEQ ID NO: 2 = The amino acid sequence of the
human MBNL1 protein, isoform b (GenBank
Accession No. NP_997175.1).
MAVSVTPIRDTKWLTLEVCREFQRGTCSRPDTECKFAHPSKSCQVENGRVIACFDSLK

GRCSRENCKYLHPPPHLKTQLEINGRNNLIQQKNMAMLAQQMQLANAMMPGAPLQP

VPMFSVAPSLATNASAAAFNPYLGPVSPSLVPAEILPTAPMLVTGNPGVPVPAAAAAA

AQKLMRTDRLEVCREYQRGNCNRGENDCRFAHPADSTMIDTNDNTVTVCMDYIKGR

CSREKCKYFHPPAHLQAKIKAAQYQVNQAAAAQAAATAAAMGIPQAVLPPLPKRPAL
```

-continued
EKTNGATAVFNTGIFQYQQALANMQLQQHTAFLPPVPMHGATPATVSAATTSATSV

PFAATATANQIPIISAEHLTSHKYVTQM

SEQ ID NO: 3 = The amino acid sequence of the
human MBNL1 protein, isoform c (GenBank
Accession No. NP_997176.1).
MAVSVTPIRDTKWLTLEVCREFQRGTCSRPDTECKFAHPSKSCQVENGRVIACFDSLK

GRCSRENCKYLHPPPHLKTQLEINGRNNLIQQKNMAMLAQQMQLANAMMPGAPLQP

VPMFSVAPSLATNASAAAFNPYLGPVSPSLVPAEILPTAPMLVTGNPGVPVPAAAAAA

AQKLMRTDRLEVCREYQRGNCNRGENDCRFAHPADSTMIDTNDNTVTVCMDYIKGR

CSREKCKYFHPPAHLQAKIKAAQYQVNQAAAAQAAATAAAMTQSAVKSLKRPLEAT

FDLGIPQAVLPPLPKRPALEKTNGATAVFNTGIFQYQQALANMQLQQHTAFLPPVPMV

HGATPATVSAATTSATSVPFAATATANQIPIISAEHLTSHKYVTQM

SEQ ID NO: 4 = The amino acid sequence of the
human MBNL1 protein, isoform d (GenBank
Accession No. NP_997177.1).
MAVSVTPIRDTKWLTLEVCREFQRGTCSRPDTECKFAHPSKSCQVENGRVIACFDSLK

GRCSRENCKYLHPPPHLKTQLEINGRNNLIQQKNMAMLAQQMQLANAMMPGAPLQP

VVCREYQRGNCNRGENDCRFAHPADSTMIDTNDNTVTVCMDYIKGRCSREKCKYFH

PPAHLQAKIKAAQYQVNQAAAAQAAATAAAMGIPQAVLPPLPKRPALEKTNGATAVF

NTGIFQYQQALANMQLQQHTAFLPPVPMVHGATPATVSAATTSATSVPFAATATANQ

IPIISAEHLTSHKYVTQM

SEQ ID NO: 5 = The amino acid sequence of the
human MBNL1 protein, isoform e (GenBank
Accession No. NP_997178.1).
MAVSVTPIRDTKWLTLEVCREFQRGTCSRPDTECKFAHPSKSCQVENGRVIACFDSLK

GRCSRENCKYLHPPPHLKTQLEINGRNNLIQQKNMAMLAQQMQLANAMMPGAPLQP

VVCREYQRGNCNRGENDCRFAHPADSTMIDTNDNTVTVCMDYIKGRCSREKCKYFH

PPAHLQAKIKAAQYQVNQAAAAQAAATAAAMGIPQAVLPPLPKRPALEKTNGATAVF

NTGIFQYQQALANMQLQQHTAFLPPGSILCMTPATSVVPMHGATPATVSAATTSATS

VPFAATATANQIPIISAEHLTSHKYVTQM

SEQ ID NO: 6 = The amino acid sequence of the
human MBNL1 protein, isoform f (GenBank
Accession No. NP_997179.1).
MAVSVTPIRDTKWLTLEVCREFQRGTCSRPDTECKFAHPSKSCQVENGRVIACFDSLK

GRCSRENCKYLHPPPHLKTQLEINGRNNLIQQKNMAMLAQQMQLANAMMPGAPLQP

VPMFSVAPSLATNASAAAFNPYLGPVSPSLVPAEILPTAPMLVTGNPGVPVPAAAAAA

AQKLMRTDRLEVCREYQRGNCNRGENDCRFAHPADSTMIDTNDNTVTVCMDYIKGR

CSREKCKYFHPPAHLQAKIKAAQYQVNQAAAAQAAATAAAMFPWCTVLRQPLCPQQ

QHLPQVFPSLQQPQPTSPILDASTLLGATSCPAAAGKMIPIISAEHLTSHKYVTQM

SEQ ID NO: 7 = The amino acid sequence of the
human MBNL1 protein, isoform g (GenBank
Accession No. NP_997180.1).
MAVSVTPIRDTKWLTLEVCREFQRGTCSRPDTECKFAHPSKSCQVENGRVIACFDSLK

GRCSRENCKYLHPPPHLKTQLEINGRNNLIQQKNMAMLAQQMQLANAMMPGAPLQP

VPMFSVAPSLATNASAAAFNPYLGPVSPSLVPAEILPTAPMLVTGNPGVPVPAAAAAA

AQKLMRTDRLEVCREYQRGNCNRGENDCRFAHPADSTMIDTNDNTVTVCMDYIKGR

CSREKCKYFHPPAHLQAKIKAAQYQVNQAAAAQAAATAAAMGIPQAVLPPLPKRPAL

EKTNGATAVFNTGIFQYQQALANMQLQQHTAFLPPGSILCMTPATSVDTHNICRTSD

-continued

SEQ ID NO: 8 = The amino acid sequence of the
human MBNL2 protein, isoform 1 (GenBank
Accession No. NP_659002.1).
MALNVAPVRDTKWLTLEVCRQFQRGTCSRSDEECKFAHPPKSCQVENGRVIACFDSL

KGRCSRENCKYLHPPTHLKTQLEINGRNNLIQQKTAAAMLAQQMQFMFPGTPLHPVP

TFPVGPAIGTNTAISFAPYLAPVTPGVGLVPTEILPTTPVIVPGSPPVTVPGSTATQKLLR

TDKLEVCREFQRGNCARGETDCRFAHPADSTMIDTSDNTVTVCMDYIKGRCMREKCK

YFHPPAHLQAKIKAAQHQANQAAVAAQAAAAATVMAFPPGALHPLPKRQALEKSN

GTSAVFNPSVLHYQQALTSAQLQQHAAFIPTGSVLCMTPATSIVPMMHSATSATVSAA

TTPATSVPFAATATANQIILK

SEQ ID NO: 9 = The amino acid sequence of the
human MBNL2 protein, isoform 3 (GenBank
Accession No. NP_997187.1).
MALNVAPVRDTKWLTLEVCRQFQRGTCSRSDEECKFAHPPKSCQVENGRVIACFDSL

KGRCSRENCKYLHPPTHLKTQLEINGRNNLIQQKTAAAMLAQQMQFMFPGTPLHPVP

TFPVGPAIGTNTAISFAPYLAPVTPGVGLVPTEILPTTPVIVPGSPPVTVPGSTATQKLLR

TDKLEVCREFQRGNCARGETDCRFAHPADSTMIDTSDNTVTVCMDYIKGRCMREKCK

YFHPPAHLQAKIKAAQHQANQAAVAAQAAAAATVMAFPPGALHPLPKRQALEKSN

GTSAVFNPSVLHYQQALTSAQLQQHAAFIPTDNSEIISRNGMECQESALRITKHCYCTY

YPVSSSIELPQTAC

SEQ ID NO: 10 = The amino acid sequence of the
human MBNL3 protein, isoform G (GenBank
Accession No. NP_060858.2).
MTAVNVALIRDTKWLTLEVCREFQRGTCSRADADCKFAHPPRVCHVENGRVVACFD

SLKGRCTRENCKYLHPPPHLKTQLEINGRNNLIQQKTAAAMFAQQMQLMLQNAQMS

SLGSFPMTPSIPANPPMAFNPYIPHPGMGLVPAELVPNTPVLIPGNPPLAMPGAVGPKL

MRSDKLEVCREFQRGNCTRGENDCRYAHPTDASMIEASDNTVTICMDYIKGRCSREK

CKYFHPPAHLQARLKAAHHQMNHSAASAMALQPGTLQLIPKRSALEKPNGATPVFNP

TVFHCQQALTNLQLPQPAFIPAGPILCMAPASNIVPMMHGATPTTVSAATTPATSVPFA

APTTGNQLKF

SEQ ID NO: 11 = The amino acid sequence of the
human MBNL3 protein, isoform R (GenBank
Accession No. NP_597846.1).
MTAVNVALIRDTKWLTLEVCREFQRGTCSRADADCKFAHPPRVCHVENGRVVACFD

SLKGRCTRENCKYLHPPPHLKTQLEINGRNNLIQQKTAAAMFAQQMQLMLQNAQMS

SLGSFPMTPSIPANPPMAFNPYIPHPGMGLVPAELVPNTPVLIPGNPPLAMPGAVGPKL

MRSDKLEVCREFQRGNCTRGENDCRYAHPTDASMIEASDNTVTICMDYIKGRCSREK

CKYFHPPAHLQARLKAAHHQMNHSAASAMALTNLQLPQPAFIPAGPILCMAPASNIVP

MMHGATPTTVSAATTPATSVPFAAPTTGNQIPQLSIDELNSSMFVSQM

SEQ ID NO: 12 = 3E10 D31Q Variable Heavy Chain
EVQLVESGGGLVKPGGSRKLSCAASGFTFSNYGMHWVRQAPEKGLEWVAYISSGSST

IYYADTVKGRFTISRDNAKNTLFLQMTSLRSEDTAMYYCARRGLLLDYWGQGTTLTV

SS

SEQ ID NO: 13 = Linker
GGGGSGGGGSGGGGS

SEQ ID NO: 14 = 3E10 Variable Light Chain
DIVLTQSPASLAVSLGQRATISCRASKSVSTSSYSYMHWYQQKPGQPPKLLIKYASYLE

SGVPARFSGSGSGTDFHLNIHPVEEEDAATYYCQHSREFPWTFGGGTKLELK

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

I claim:

1. A chimeric polypeptide comprising: (i) a functional fragment of an MBNL1 polypeptide, wherein the MBNL1 polypeptide comprises an amino acid sequence that is at least 95% identical to SEQ ID NO: 3, and wherein the functional fragment comprises amino acids 1-248 of the MBNL1 polypeptide, and (ii) a targeting moiety, wherein the targeting moiety comprises an antibody or antigen-binding fragment, wherein the targeting moiety transits cellular membranes via an equilibrative nucleoside transporter 2 (ENT2) transporter; and wherein the chimeric polypeptide is capable of binding CUG repeats.

2. The chimeric polypeptide of claim 1, wherein the antibody or antigen-binding fragment comprises a heavy chain variable domain (VH) and a light chain variable domain (VL), wherein the VH comprises an amino acid sequence that is at least 90% identical to the amino acid sequence set forth in SEQ ID NO: 12, and the VL comprises an amino acid sequence that is at least 90% identical to the amino acid sequence set forth in SEQ ID NO: 14, or which is a humanized antibody or antigen-binding fragment thereof.

3. The chimeric polypeptide of claim 2, wherein the VH comprises an amino acid sequence that is at least 95% identical to the amino acid sequence set forth in SEQ ID NO: 12, and the VL comprises an amino acid sequence that is at least 95% identical to the amino acid sequence set forth in SEQ ID NO: 14, or which is a humanized antibody or antigen-binding fragment thereof.

4. The chimeric polypeptide of claim 3, wherein the VH comprises the amino acid sequence set forth in SEQ ID NO: 12, and the VL comprises the amino acid sequence set forth in SEQ ID NO: 14, or which is a humanized antibody or antigen-binding fragment thereof.

5. The chimeric polypeptide of claim 1 or 4, wherein the functional fragment of the MBNL1 polypeptide is at least 250 amino acids in length and lacks a portion of the C-terminus of SEQ ID NO: 3; and wherein the targeting moiety is a Fab' fragment.

6. The chimeric polypeptide of claim 1 or 4, comprising a functional fragment of an MBNL1 polypeptide, wherein the MBNL1 polypeptide comprises the amino acid sequence set forth in SEQ ID NO: 3.

7. The chimeric polypeptide of claim 6, wherein the targeting moiety is a Fab' fragment.

8. The chimeric polypeptide of claim 6, wherein the targeting moiety is an antibody.

9. A composition comprising the chimeric polypeptide of claim 6, and a pharmaceutically acceptable carrier.

10. The chimeric polypeptide of claim 6, wherein the functional fragment of the MBNL1 polypeptide is at least 250 amino acids in length and lacks a portion of the C-terminus of SEQ ID NO: 3.

11. The chimeric polypeptide of claim 10, wherein the targeting moiety is a Fab' fragment.

12. The chimeric polypeptide of claim 11, wherein the functional fragment of the MBNL1 polypeptide comprising amino acid residues 1-250 of SEQ ID NO: 3.

13. The chimeric polypeptide of claim 10, wherein the targeting moiety is an antibody.

14. A composition comprising the chimeric polypeptide of claim 10, and a pharmaceutically acceptable carrier.

15. The chimeric polypeptide of claim 10, wherein the functional fragment of the MBNL1 polypeptide comprising amino acid residues 1-250 of SEQ ID NO: 3.

16. The chimeric polypeptide of claim 1, wherein the functional fragment of the MBNL1 polypeptide lacks a portion of the C-terminus.

17. The chimeric polypeptide of claim 1, wherein the targeting moiety comprises an antibody.

18. The chimeric polypeptide of claim 1, wherein the targeting moiety is an antigen-binding fragment.

19. The chimeric polypeptide of claim 18, wherein the antigen-binding fragment is a single chain Fv fragment (scFv).

20. The chimeric polypeptide of claim 18, wherein the antigen-binding fragment is a Fab' fragment.

21. The chimeric polypeptide of claim 1, wherein the chimeric polypeptide is produced by chemically conjugating the functional fragment of the MBNL1 polypeptide to the targeting moiety.

22. The chimeric polypeptide of claim 1, wherein the chimeric polypeptide is produced by a recombinant vector encoding both the functional fragment of the MBNL1 polypeptide and the targeting moiety.

23. The chimeric polypeptide of claim 1, wherein the antibody or antigen-binding fragment thereof is an antigen binding fragment of 3E10.

24. The chimeric polypeptide of claim 1, wherein the chimeric polypeptide is produced recombinantly to recombinantly conjugate the functional fragment of the MBNL1 polypeptide to the targeting moiety.

25. The chimeric polypeptide of claim 24, wherein the chimeric polypeptide is produced in a prokaryotic or eukaryotic cell.

26. The chimeric polypeptide of claim 1, wherein the functional fragment of the MBNL1 polypeptide is conjugated or joined to the targeting moiety by a linker.

27. The chimeric polypeptide of claim 26, wherein the targeting moiety is conjugated to the N-terminal or C-terminal amino acid of the functional fragment of the MBNL1 polypeptide.

28. The chimeric polypeptide of claim 1, wherein the functional fragment of the MBNL1 polypeptide is conjugated or joined directly to the targeting moiety.

29. The chimeric polypeptide of claim 1, wherein the targeting moiety promotes transport into muscle cells.

30. The chimeric polypeptide of claim 1, wherein the targeting moiety promotes transport into neurons.

31. A composition comprising the chimeric polypeptide of claim 1, and a pharmaceutically acceptable carrier.

32. A nucleic acid construct, comprising a nucleotide sequence that encodes a functional fragment of an MBNL1 polypeptide, wherein the MBNL1 polypeptide comprises an amino acid sequence that is at least 95% identical to SEQ ID NO: 3, wherein the functional fragment comprises amino acids 1-248 of the MBNL1 polypeptide, and wherein the functional fragment is operably linked to a nucleotide sequence that encodes a targeting moiety, wherein the targeting moiety comprises an antibody or antigen-binding fragment, wherein the targeting moiety transits cellular membranes via an equilibrative nucleoside transporter 2 (ENT2) transporter;
wherein the nucleic acid construct encodes a chimeric polypeptide having MBNL biological activity and having the targeting activity of the targeting moiety; and wherein the chimeric polypeptide is capable of binding CUG repeats.

33. The nucleic acid construct of claim 32, wherein the targeting moiety promotes transport into muscle cells or neurons.

34. The nucleic acid construct of claim 32, wherein the functional fragment of the MBNL polypeptide is at least 250 amino acids in length and lacks a portion of the C-terminus of the MBNL1 polypeptide; and wherein the targeting moiety is a Fab' fragment.

35. The nucleic acid construct of claim 34, wherein the antibody or antigen-binding fragment comprises a heavy chain variable domain (VH) and a light chain variable domain (VL), wherein the VH comprises the amino acid sequence set forth in SEQ ID NO: 12, and the VL comprises the amino acid sequence set forth in SEQ ID NO: 14, or which is a humanized antibody or antigen-binding fragment thereof.

36. The nucleic acid of claim 35, wherein the chimeric polypeptide comprises a functional fragment of an MBNL1 polypeptide, wherein the MBNL1 polypeptide comprises the amino acid sequence set forth in SEQ ID NO: 3.

37. The nucleic acid of claim 36, wherein the functional fragment of the MBNL1 polypeptide is at least 250 amino acids in length and lacks a portion of the C-terminus of SEQ ID NO: 3.

38. The nucleic acid of claim 37, wherein the targeting moiety is a Fab' fragment.

39. The nucleic acid of claim 37, wherein the targeting moiety is an antibody.

40. The nucleic acid of claim 36, wherein the targeting moiety is a Fab' fragment.

41. The nucleic acid of claim 36, wherein the targeting moiety is an antibody.

42. A method of delivering a chimeric polypeptide into a cell, comprising contacting a cell with a chimeric polypeptide, which chimeric polypeptide comprises: (i) a functional fragment of an MBNL1 polypeptide, wherein the MBNL1 polypeptide comprises an amino acid sequence that is at least 95% identical to SEQ ID NO: 3, and wherein the functional fragment comprises amino acids 1-248 of the MBNL1 polypeptide, and (ii) a targeting moiety, wherein the targeting moiety comprises an antibody or antigen-binding fragment, wherein the targeting moiety transits cellular membranes via an equilibrative nucleoside transporter 2 (ENT2) transporter; and wherein the chimeric polypeptide is capable of binding CUG repeats.

43. The method of claim 42, wherein the antibody or antigen-binding fragment is an antigen-binding fragment.

44. The method of claim 43, wherein the antigen-binding fragment is a Fab' fragment.

45. The method of claim 42, wherein the cell is a muscle cell.

46. The method of claim 45, wherein the muscle cell is a skeletal muscle cell.

47. The method of claim 45, wherein the muscle cell is a cardiac muscle cell.

48. The method of claim 42, wherein the cell is a neuron.

49. The method of claim 42, wherein the chimeric polypeptide is produced by chemically conjugating the functional fragment of the MBNL polypeptide to the targeting moiety.

50. The method of claim 42, wherein the functional fragment of the MBNL1 polypeptide is at least 250 amino acids in length and lacks a portion of the C-terminus of SEQ ID NO: 3; wherein the antibody or antigen-binding fragment is a humanized variant of an antibody or antigen-binding fragment comprising a heavy chain variable domain (VH) and a light chain variable domain (VL), wherein the VH comprises the amino acid sequence set forth in SEQ ID NO: 12 or a humanized variant thereof, and the VL comprises the amino acid sequence set forth in SEQ ID NO: 14 or a humanized variant thereof.

51. A chimeric polypeptide comprising: (i) a functional fragment of an MBNL1 polypeptide, wherein the functional fragment comprises amino acids 1-248 of a human MBNL1 polypeptide, and (ii) a targeting moiety, wherein the targeting moiety comprises an antibody or antigen-binding fragment, wherein the targeting moiety transits cellular membranes via an equilibrative nucleoside transporter 2 (ENT2) transporter; and wherein the chimeric polypeptide is capable of binding CUG repeats.

52. The chimeric polypeptide of claim 51, wherein the antibody or antigen-binding fragment comprises a heavy chain variable domain (VH) and a light chain variable domain (VL), wherein the VH comprises an amino acid sequence that is at least 90% identical to the amino acid sequence set forth in SEQ ID NO: 12, and the VL comprises an amino acid sequence that is at least 90% identical to the amino acid sequence set forth in SEQ ID NO: 14, or which is a humanized antibody or antigen-binding fragment thereof.

53. The chimeric polypeptide of claim 52, wherein the VH comprises the amino acid sequence set forth in SEQ ID NO: 12, and the VL comprises the amino acid sequence set forth in SEQ ID NO: 14, or which is a humanized antibody or antigen-binding fragment thereof.

54. The chimeric polypeptide of claim 53, wherein the targeting moiety comprises an antibody.

55. The chimeric polypeptide of claim 53, wherein the targeting moiety is a Fab' fragment.

56. The chimeric polypeptide of claim 51, wherein the functional fragment of the MBNL1 polypeptide is at least 250 amino acids in length and lacks a portion of the C-terminus of a human MBNL1 polypeptide.

* * * * *

```
                        SEQUENCE LISTING

<160> NUMBER OF SEQ ID NOS: 17

<210> SEQ ID NO 1
<211> LENGTH: 382
<212> TYPE: PRT
<213> ORGANISM: Homo sapiens

<400> SEQUENCE: 1

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Thr Ala Ala Met Gly Ile Pro
            260                 265                 270

Gln Ala Val Leu Pro Pro Leu Pro Lys Arg Pro Ala Leu Glu Lys Thr
        275                 280                 285

Asn Gly Ala Thr Ala Val Phe Asn Thr Gly Ile Phe Gln Tyr Gln Gln
    290                 295                 300

Ala Leu Ala Asn Met Gln Leu Gln Gln His Thr Ala Phe Leu Pro Pro
305                 310                 315                 320
```

```
Gly Ser Ile Leu Cys Met Thr Pro Ala Thr Ser Val Pro Met Val
            325                 330                 335

His Gly Ala Thr Pro Ala Thr Val Ser Ala Ala Thr Thr Ser Ala Thr
                340                 345                 350

Ser Val Pro Phe Ala Ala Thr Ala Thr Ala Asn Gln Ile Pro Ile Ile
            355                 360                 365

Ser Ala Glu His Leu Thr Ser His Lys Tyr Val Thr Gln Met
370                 375                 380

<210> SEQ ID NO 2
<211> LENGTH: 370
<212> TYPE: PRT
<213> ORGANISM: Homo sapiens

<400> SEQUENCE: 2

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
                20                  25                  30

Glu Cys Lys Phe Ala His Pro Ser Lys Ser Cys Gln Val Glu Asn Gly
            35                  40                  45

Arg Val Ile Ala Cys Phe Asp Ser Leu Lys Gly Arg Cys Ser Arg Glu
50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
            115                 120                 125

Ser Ala Ala Ala Phe Asn Pro Tyr Leu Gly Pro Val Ser Pro Ser Leu
130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
            195                 200                 205

Thr Met Ile Asp Thr Asn Asp Asn Thr Val Thr Val Cys Met Asp Tyr
            210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Thr Ala Ala Ala Met Gly Ile Pro
            260                 265                 270

Gln Ala Val Leu Pro Pro Leu Pro Lys Arg Pro Ala Leu Glu Lys Thr
            275                 280                 285

Asn Gly Ala Thr Ala Val Phe Asn Thr Gly Ile Phe Gln Tyr Gln Gln
            290                 295                 300

Ala Leu Ala Asn Met Gln Leu Gln Gln His Thr Ala Phe Leu Pro Pro
305                 310                 315                 320
```

Val Pro Met Val His Gly Ala Thr Pro Ala Thr Val Ser Ala Ala Thr
        325                 330                 335

Thr Ser Ala Thr Ser Val Pro Phe Ala Ala Thr Ala Thr Ala Asn Gln
        340                 345                 350

Ile Pro Ile Ile Ser Ala Glu His Leu Thr Ser His Lys Tyr Val Thr
        355                 360                 365

Gln Met
    370

<210> SEQ ID NO 3
<211> LENGTH: 388
<212> TYPE: PRT
<213> ORGANISM: Homo sapiens

<400> SEQUENCE: 3

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Ala Thr Ala Ala Ala Met Thr Gln Ser
            260                 265                 270

Ala Val Lys Ser Leu Lys Arg Pro Leu Glu Ala Thr Phe Asp Leu Gly
        275                 280                 285

Ile Pro Gln Ala Val Leu Pro Pro Leu Pro Lys Arg Pro Ala Leu Glu
    290                 295                 300

Lys Thr Asn Gly Ala Thr Ala Val Phe Asn Thr Gly Ile Phe Gln Tyr
305                 310                 315                 320

```
Gln Gln Ala Leu Ala Asn Met Gln Leu Gln Gln His Thr Ala Phe Leu
                325                 330                 335

Pro Pro Val Pro Met Val His Gly Ala Thr Pro Ala Thr Val Ser Ala
            340                 345                 350

Ala Thr Thr Ser Ala Thr Ser Val Pro Phe Ala Ala Thr Ala Thr Ala
            355                 360                 365

Asn Gln Ile Pro Ile Ile Ser Ala Glu His Leu Thr Ser His Lys Tyr
            370                 375                 380

Val Thr Gln Met
385

<210> SEQ ID NO 4
<211> LENGTH: 302
<212> TYPE: PRT
<213> ORGANISM: Homo sapiens

<400> SEQUENCE: 4

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Val Cys Arg Glu Tyr Gln Arg Gly Asn Cys Asn Arg Gly
        115                 120                 125

Glu Asn Asp Cys Arg Phe Ala His Pro Ala Asp Ser Thr Met Ile Asp
    130                 135                 140

Thr Asn Asp Asn Thr Val Thr Val Cys Met Asp Tyr Ile Lys Gly Arg
145                 150                 155                 160

Cys Ser Arg Glu Lys Cys Lys Tyr Phe His Pro Pro Ala His Leu Gln
                165                 170                 175

Ala Lys Ile Lys Ala Ala Gln Tyr Gln Val Asn Gln Ala Ala Ala Ala
            180                 185                 190

Gln Ala Ala Ala Thr Ala Ala Ala Met Gly Ile Pro Gln Ala Val Leu
        195                 200                 205

Pro Pro Leu Pro Lys Arg Pro Ala Leu Glu Lys Thr Asn Gly Ala Thr
    210                 215                 220

Ala Val Phe Asn Thr Gly Ile Phe Gln Tyr Gln Gln Ala Leu Ala Asn
225                 230                 235                 240

Met Gln Leu Gln Gln His Thr Ala Phe Leu Pro Pro Val Pro Met Val
                245                 250                 255

His Gly Ala Thr Pro Ala Thr Val Ser Ala Ala Thr Ser Ala
            260                 265                 270

Ser Val Pro Phe Ala Ala Thr Ala Thr Ala Asn Gln Ile Pro Ile Ile
        275                 280                 285

Ser Ala Glu His Leu Thr Ser His Lys Tyr Val Thr Gln Met
    290                 295                 300
```

<210> SEQ ID NO 5
<211> LENGTH: 314
<212> TYPE: PRT
<213> ORGANISM: Homo sapiens

<400> SEQUENCE: 5

```
Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Val Cys Arg Glu Tyr Gln Arg Gly Asn Cys Asn Arg Gly
        115                 120                 125

Glu Asn Asp Cys Arg Phe Ala His Pro Ala Asp Ser Thr Met Ile Asp
    130                 135                 140

Thr Asn Asp Asn Thr Val Thr Val Cys Met Asp Tyr Ile Lys Gly Arg
145                 150                 155                 160

Cys Ser Arg Glu Lys Cys Lys Tyr Phe His Pro Pro Ala His Leu Gln
                165                 170                 175

Ala Lys Ile Lys Ala Ala Gln Tyr Gln Val Asn Gln Ala Ala Ala Ala
            180                 185                 190

Gln Ala Ala Ala Thr Ala Ala Ala Met Gly Ile Pro Gln Ala Val Leu
        195                 200                 205

Pro Pro Leu Pro Lys Arg Pro Ala Leu Glu Lys Thr Asn Gly Ala Thr
    210                 215                 220

Ala Val Phe Asn Thr Gly Ile Phe Gln Tyr Gln Gln Ala Leu Ala Asn
225                 230                 235                 240

Met Gln Leu Gln Gln His Thr Ala Phe Leu Pro Pro Gly Ser Ile Leu
                245                 250                 255

Cys Met Thr Pro Ala Thr Ser Val Val Pro Met Val His Gly Ala Thr
            260                 265                 270

Pro Ala Thr Val Ser Ala Ala Thr Thr Ser Ala Thr Ser Val Pro Phe
        275                 280                 285

Ala Ala Thr Ala Thr Ala Asn Gln Ile Pro Ile Ile Ser Ala Glu His
    290                 295                 300

Leu Thr Ser His Lys Tyr Val Thr Gln Met
305                 310
```

<210> SEQ ID NO 6
<211> LENGTH: 340
<212> TYPE: PRT
<213> ORGANISM: Homo sapiens

```
<400> SEQUENCE: 6

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Phe Asn Pro Tyr Leu Gly Pro Val Ser Pro Ser Leu
130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Thr Ala Ala Met Phe Pro Trp
            260                 265                 270

Cys Thr Val Leu Arg Gln Pro Leu Cys Pro Gln Gln Gln His Leu Pro
        275                 280                 285

Gln Val Phe Pro Ser Leu Gln Gln Pro Gln Pro Thr Ser Pro Ile Leu
    290                 295                 300

Asp Ala Ser Thr Leu Leu Gly Ala Thr Ser Cys Pro Ala Ala Gly
305                 310                 315                 320

Lys Met Ile Pro Ile Ile Ser Ala Glu His Leu Thr Ser His Lys Tyr
                325                 330                 335

Val Thr Gln Met
            340

<210> SEQ ID NO 7
<211> LENGTH: 342
<212> TYPE: PRT
<213> ORGANISM: Homo sapiens
```

-continued

<400> SEQUENCE: 7

```
Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Thr Ala Ala Ala Met Gly Ile Pro
            260                 265                 270

Gln Ala Val Leu Pro Pro Leu Pro Lys Arg Pro Ala Leu Glu Lys Thr
        275                 280                 285

Asn Gly Ala Thr Ala Val Phe Asn Thr Gly Ile Phe Gln Tyr Gln Gln
    290                 295                 300

Ala Leu Ala Asn Met Gln Leu Gln Gln His Thr Ala Phe Leu Pro Pro
305                 310                 315                 320

Gly Ser Ile Leu Cys Met Thr Pro Ala Thr Ser Val Asp Thr His Asn
                325                 330                 335

Ile Cys Arg Thr Ser Asp
            340
```

<210> SEQ ID NO 8
<211> LENGTH: 367
<212> TYPE: PRT
<213> ORGANISM: Homo sapiens

<400> SEQUENCE: 8

```
Met Ala Leu Asn Val Ala Pro Val Arg Asp Thr Lys Trp Leu Thr Leu
1               5                   10                  15
Glu Val Cys Arg Gln Phe Gln Arg Gly Thr Cys Ser Arg Ser Asp Glu
            20                  25                  30
Glu Cys Lys Phe Ala His Pro Pro Lys Ser Cys Gln Val Glu Asn Gly
        35                  40                  45
Arg Val Ile Ala Cys Phe Asp Ser Leu Lys Gly Arg Cys Ser Arg Glu
    50                  55                  60
Asn Cys Lys Tyr Leu His Pro Pro Thr His Leu Lys Thr Gln Leu Glu
65                  70                  75                  80
Ile Asn Gly Arg Asn Asn Leu Ile Gln Gln Lys Thr Ala Ala Ala Met
                85                  90                  95
Leu Ala Gln Gln Met Gln Phe Met Phe Pro Gly Thr Pro Leu His Pro
            100                 105                 110
Val Pro Thr Phe Pro Val Gly Pro Ala Ile Gly Thr Asn Thr Ala Ile
        115                 120                 125
Ser Phe Ala Pro Tyr Leu Ala Pro Val Thr Pro Gly Val Gly Leu Val
    130                 135                 140
Pro Thr Glu Ile Leu Pro Thr Thr Pro Val Ile Val Pro Gly Ser Pro
145                 150                 155                 160
Pro Val Thr Val Pro Gly Ser Thr Ala Thr Gln Lys Leu Leu Arg Thr
                165                 170                 175
Asp Lys Leu Glu Val Cys Arg Glu Phe Gln Arg Gly Asn Cys Ala Arg
            180                 185                 190
Gly Glu Thr Asp Cys Arg Phe Ala His Pro Ala Asp Ser Thr Met Ile
        195                 200                 205
Asp Thr Ser Asp Asn Thr Val Thr Val Cys Met Asp Tyr Ile Lys Gly
    210                 215                 220
Arg Cys Met Arg Glu Lys Cys Lys Tyr Phe His Pro Pro Ala His Leu
225                 230                 235                 240
Gln Ala Lys Ile Lys Ala Ala Gln His Gln Ala Asn Gln Ala Ala Val
                245                 250                 255
Ala Ala Gln Ala Ala Ala Ala Ala Thr Val Met Ala Phe Pro Pro Pro
            260                 265                 270
Gly Ala Leu His Pro Leu Pro Lys Arg Gln Ala Leu Glu Lys Ser Asn
        275                 280                 285
Gly Thr Ser Ala Val Phe Asn Pro Ser Val Leu His Tyr Gln Gln Ala
    290                 295                 300
Leu Thr Ser Ala Gln Leu Gln Gln His Ala Ala Phe Ile Pro Thr Gly
305                 310                 315                 320
Ser Val Leu Cys Met Thr Pro Ala Thr Ser Ile Val Pro Met Met His
                325                 330                 335
Ser Ala Thr Ser Ala Thr Val Ser Ala Ala Thr Thr Pro Ala Thr Ser
            340                 345                 350
Val Pro Phe Ala Ala Thr Ala Thr Ala Asn Gln Ile Ile Leu Lys
        355                 360                 365
```

<210> SEQ ID NO 9
<211> LENGTH: 361
<212> TYPE: PRT
<213> ORGANISM: Homo sapiens

<400> SEQUENCE: 9

```
Met Ala Leu Asn Val Ala Pro Val Arg Asp Thr Lys Trp Leu Thr Leu
1               5                   10                  15
Glu Val Cys Arg Gln Phe Gln Arg Gly Thr Cys Ser Arg Ser Asp Glu
            20                  25                  30
Glu Cys Lys Phe Ala His Pro Pro Lys Ser Cys Gln Val Glu Asn Gly
        35                  40                  45
Arg Val Ile Ala Cys Phe Asp Ser Leu Lys Gly Arg Cys Ser Arg Glu
    50                  55                  60
Asn Cys Lys Tyr Leu His Pro Pro Thr His Leu Lys Thr Gln Leu Glu
65                  70                  75                  80
Ile Asn Gly Arg Asn Asn Leu Ile Gln Gln Lys Thr Ala Ala Ala Met
                85                  90                  95
Leu Ala Gln Gln Met Gln Phe Met Phe Pro Gly Thr Pro Leu His Pro
            100                 105                 110
Val Pro Thr Phe Pro Val Gly Pro Ala Ile Gly Thr Asn Thr Ala Ile
        115                 120                 125
Ser Phe Ala Pro Tyr Leu Ala Pro Val Thr Pro Gly Val Gly Leu Val
    130                 135                 140
Pro Thr Glu Ile Leu Pro Thr Thr Pro Val Ile Val Pro Gly Ser Pro
145                 150                 155                 160
Pro Val Thr Val Pro Gly Ser Thr Ala Thr Gln Lys Leu Leu Arg Thr
                165                 170                 175
Asp Lys Leu Glu Val Cys Arg Glu Phe Gln Arg Gly Asn Cys Ala Arg
            180                 185                 190
Gly Glu Thr Asp Cys Arg Phe Ala His Pro Ala Asp Ser Thr Met Ile
        195                 200                 205
Asp Thr Ser Asp Asn Thr Val Thr Val Cys Met Asp Tyr Ile Lys Gly
    210                 215                 220
Arg Cys Met Arg Glu Lys Cys Lys Tyr Phe His Pro Pro Ala His Leu
225                 230                 235                 240
Gln Ala Lys Ile Lys Ala Ala Gln His Gln Ala Asn Gln Ala Ala Val
                245                 250                 255
Ala Ala Gln Ala Ala Ala Ala Ala Thr Val Met Ala Phe Pro Pro Pro
            260                 265                 270
Gly Ala Leu His Pro Leu Pro Lys Arg Gln Ala Leu Glu Lys Ser Asn
        275                 280                 285
Gly Thr Ser Ala Val Phe Asn Pro Ser Val Leu His Tyr Gln Gln Ala
    290                 295                 300
Leu Thr Ser Ala Gln Leu Gln Gln His Ala Ala Phe Ile Pro Thr Asp
305                 310                 315                 320
Asn Ser Glu Ile Ile Ser Arg Asn Gly Met Glu Cys Gln Glu Ser Ala
                325                 330                 335
Leu Arg Ile Thr Lys His Cys Tyr Cys Thr Tyr Tyr Pro Val Ser Ser
            340                 345                 350
Ser Ile Glu Leu Pro Gln Thr Ala Cys
        355                 360
```

<210> SEQ ID NO 10
<211> LENGTH: 354
<212> TYPE: PRT
<213> ORGANISM: Homo sapiens -continued

<400> SEQUENCE: 10

```
Met Thr Ala Val Asn Val Ala Leu Ile Arg Asp Thr Lys Trp Leu Thr
1               5                   10                  15

Leu Glu Val Cys Arg Glu Phe Gln Arg Gly Thr Cys Ser Arg Ala Asp
            20                  25                  30

Ala Asp Cys Lys Phe Ala His Pro Pro Arg Val Cys His Val Glu Asn
        35                  40                  45

Gly Arg Val Val Ala Cys Phe Asp Ser Leu Lys Gly Arg Cys Thr Arg
50                  55                  60

Glu Asn Cys Lys Tyr Leu His Pro Pro His Leu Lys Thr Gln Leu
65                  70                  75                  80

Glu Ile Asn Gly Arg Asn Asn Leu Ile Gln Gln Lys Thr Ala Ala Ala
                85                  90                  95

Met Phe Ala Gln Gln Met Gln Leu Met Leu Gln Asn Ala Gln Met Ser
            100                 105                 110

Ser Leu Gly Ser Phe Pro Met Thr Pro Ser Ile Pro Ala Asn Pro Pro
        115                 120                 125

Met Ala Phe Asn Pro Tyr Ile Pro His Pro Gly Met Gly Leu Val Pro
    130                 135                 140

Ala Glu Leu Val Pro Asn Thr Pro Val Leu Ile Pro Gly Asn Pro Pro
145                 150                 155                 160

Leu Ala Met Pro Gly Ala Val Gly Pro Lys Leu Met Arg Ser Asp Lys
                165                 170                 175

Leu Glu Val Cys Arg Glu Phe Gln Arg Gly Asn Cys Thr Arg Gly Glu
            180                 185                 190

Asn Asp Cys Arg Tyr Ala His Pro Thr Asp Ala Ser Met Ile Glu Ala
        195                 200                 205

Ser Asp Asn Thr Val Thr Ile Cys Met Asp Tyr Ile Lys Gly Arg Cys
    210                 215                 220

Ser Arg Glu Lys Cys Lys Tyr Phe His Pro Ala His Leu Gln Ala
225                 230                 235                 240

Arg Leu Lys Ala Ala His His Gln Met Asn His Ser Ala Ala Ser Ala
                245                 250                 255

Met Ala Leu Gln Pro Gly Thr Leu Gln Leu Ile Pro Lys Arg Ser Ala
            260                 265                 270

Leu Glu Lys Pro Asn Gly Ala Thr Pro Val Phe Asn Pro Thr Val Phe
        275                 280                 285

His Cys Gln Gln Ala Leu Thr Asn Leu Gln Leu Pro Gln Pro Ala Phe
    290                 295                 300

Ile Pro Ala Gly Pro Ile Leu Cys Met Ala Pro Ala Ser Asn Ile Val
305                 310                 315                 320

Pro Met Met His Gly Ala Thr Pro Thr Thr Val Ser Ala Ala Thr Thr
                325                 330                 335

Pro Ala Thr Ser Val Pro Phe Ala Ala Pro Thr Thr Gly Asn Gln Leu
            340                 345                 350

Lys Phe
```

<210> SEQ ID NO 11
<211> LENGTH: 334
<212> TYPE: PRT
<213> ORGANISM: Homo sapiens

<400> SEQUENCE: 11

Met Thr Ala Val Asn Val Ala Leu Ile Arg Asp Thr Lys Trp Leu Thr
1               5                   10                  15

Leu Glu Val Cys Arg Glu Phe Gln Arg Gly Thr Cys Ser Arg Ala Asp
            20                  25                  30

Ala Asp Cys Lys Phe Ala His Pro Pro Arg Val Cys His Val Glu Asn
        35                  40                  45

Gly Arg Val Val Ala Cys Phe Asp Ser Leu Lys Gly Arg Cys Thr Arg
    50                  55                  60

Glu Asn Cys Lys Tyr Leu His Pro Pro His Leu Lys Thr Gln Leu
65                  70                  75                  80

Glu Ile Asn Gly Arg Asn Asn Leu Ile Gln Gln Lys Thr Ala Ala
                85                  90                  95

Met Phe Ala Gln Gln Met Gln Leu Met Leu Gln Asn Ala Gln Met Ser
            100                 105                 110

Ser Leu Gly Ser Phe Pro Met Thr Pro Ser Ile Pro Ala Asn Pro Pro
            115                 120                 125

Met Ala Phe Asn Pro Tyr Ile Pro His Pro Gly Met Gly Leu Val Pro
            130                 135                 140

Ala Glu Leu Val Pro Asn Thr Pro Val Leu Ile Pro Gly Asn Pro Pro
145                 150                 155                 160

Leu Ala Met Pro Gly Ala Val Gly Pro Lys Leu Met Arg Ser Asp Lys
                165                 170                 175

Leu Glu Val Cys Arg Glu Phe Gln Arg Gly Asn Cys Thr Arg Gly Glu
            180                 185                 190

Asn Asp Cys Arg Tyr Ala His Pro Thr Asp Ala Ser Met Ile Glu Ala
            195                 200                 205

Ser Asp Asn Thr Val Thr Ile Cys Met Asp Tyr Ile Lys Gly Arg Cys
210                 215                 220

Ser Arg Glu Lys Cys Lys Tyr Phe His Pro Pro Ala His Leu Gln Ala
225                 230                 235                 240

Arg Leu Lys Ala Ala His His Gln Met Asn His Ser Ala Ala Ser Ala
                245                 250                 255

Met Ala Leu Thr Asn Leu Gln Leu Pro Gln Pro Ala Phe Ile Pro Ala
            260                 265                 270

Gly Pro Ile Leu Cys Met Ala Pro Ala Ser Asn Ile Val Pro Met Met
            275                 280                 285

His Gly Ala Thr Pro Thr Thr Val Ser Ala Ala Thr Thr Pro Ala Thr
            290                 295                 300

Ser Val Pro Phe Ala Ala Pro Thr Thr Gly Asn Gln Ile Pro Gln Leu
305                 310                 315                 320

Ser Ile Asp Glu Leu Asn Ser Ser Met Phe Val Ser Gln Met
                325                 330

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 12

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110
```

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ser Ser Leu Asn Ile Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Arg Arg Arg Arg Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
1               5
```